US009823231B1

(12) United States Patent
Steele et al.

(10) Patent No.: US 9,823,231 B1
(45) Date of Patent: Nov. 21, 2017

(54) SYSTEMS AND METHODS FOR ASSEMBLING A COLLECTION OF PEAKS CHARACTERIZING A GAS LEAK SOURCE AND SELECTING REPRESENTATIVE PEAKS FOR DISPLAY

(71) Applicant: Picarro Inc., Santa Clara, CA (US)

(72) Inventors: David Steele, San Francisco, CA (US); Sze M. Tan, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 647 days.

(21) Appl. No.: 14/319,236

(22) Filed: Jun. 30, 2014

(51) Int. Cl.
G01N 33/00 (2006.01)
G01M 3/04 (2006.01)
G01M 3/22 (2006.01)
G01N 21/3504 (2014.01)

(52) U.S. Cl.
CPC .......... *G01N 33/0062* (2013.01); *G01M 3/04* (2013.01); *G01M 3/22* (2013.01); *G01N 21/3504* (2013.01); *G01N 33/0004* (2013.01); *G01N 33/0009* (2013.01)

(58) Field of Classification Search
USPC .......................................................... 702/24
See application file for complete search history.

(56) References Cited

U.S. PATENT DOCUMENTS

| 4,690,689 A | 9/1987 | Malcosky et al. |
| 5,191,341 A | 3/1993 | Gouard et al. |
| 5,297,421 A | 3/1994 | Hosonuma et al. |

(Continued)

FOREIGN PATENT DOCUMENTS

| CA | 2339865 A1 | 7/2002 | |
| JP | 61155932 A | * 7/1986 | .............. G01M 3/20 |

OTHER PUBLICATIONS

Gifford, Frank, "Statistical Properties of a Fluctuating Plume Dispersion Model," p. 117-137, U.S. Weather Bureau Office, Oak Ridge, Tennessee. 1959; the year of publication is sufficiently earlier than the effective U.S. filed and any foreign priority date so that the particular month of publication is not in issue.

(Continued)

*Primary Examiner* — Gregory J Toatley
*Assistant Examiner* — Terence Stifter, Jr.
(74) *Attorney, Agent, or Firm* — Law Office of Andrei D Popovici, PC

(57) ABSTRACT

In some embodiments, vehicle-based natural gas leak detection methods include assembling a collection of measured concentration peaks originating from a common natural gas leak according to wind direction, wind variability and inter-peak distance data, and selecting from the collection a subset of one or more representative peaks for display. Assigning peaks to a collection may be performed according to a peak overlap condition dependent upon a scaling (overlap) factor which scales the spatial reach of a peak, and according to a wind condition which determines whether a downwind event points toward an upwind event. The scaling factor may depend on wind variability and on an orientation of an inter-peak vector relative to a representative wind direction. Peak filtering is particularly useful in urban environments, where buildings channel gas plumes and one leak may lead to sequential detections of multiple concentration peaks along a path.

31 Claims, 21 Drawing Sheets

(56) References Cited

U.S. PATENT DOCUMENTS

| | | | |
|---|---|---|---|
| 5,390,530 A | 2/1995 | Hosonuma et al. | |
| 5,946,095 A | 8/1999 | Henningsen et al. | |
| 6,282,943 B1 | 9/2001 | Sanders et al. | |
| 6,518,562 B1 | 2/2003 | Cooper et al. | |
| 6,532,801 B1* | 3/2003 | Shan | G01M 3/22 73/170.04 |
| 6,664,533 B1 | 12/2003 | van der Laan et al. | |
| 6,815,687 B1 | 11/2004 | Branch-Sullivan et al. | |
| 6,822,742 B1 | 11/2004 | Kalayeh et al. | |
| 6,995,846 B2 | 2/2006 | Kalayeh et al. | |
| 7,075,653 B1 | 7/2006 | Rutherford | |
| 7,260,507 B2 | 8/2007 | Kalayeh | |
| 7,352,463 B2 | 4/2008 | Bounaix | |
| 7,486,399 B1 | 2/2009 | Reichardt et al. | |
| 7,602,277 B1 | 10/2009 | Daly et al. | |
| 7,730,776 B2 | 6/2010 | Cornett et al. | |
| 7,934,412 B2 | 5/2011 | Prince | |
| 8,000,936 B2 | 8/2011 | Davis | |
| 8,081,112 B2 | 12/2011 | Tucker et al. | |
| 8,200,737 B2 | 6/2012 | Tarabzouni et al. | |
| 9,322,735 B1 | 4/2016 | Tan et al. | |
| 9,557,240 B1 | 1/2017 | Tan et al. | |
| 9,599,529 B1 | 3/2017 | Steele et al. | |
| 9,599,597 B1 | 3/2017 | Steele et al. | |
| 9,645,039 B1 | 5/2017 | Tan et al. | |
| 2004/0012491 A1 | 1/2004 | Kulesz et al. | |
| 2004/0263852 A1 | 12/2004 | Degtiarev et al. | |
| 2005/0038825 A1 | 2/2005 | Tarabzouni et al. | |
| 2006/0162428 A1 | 7/2006 | Hu et al. | |
| 2006/0203248 A1 | 9/2006 | Reichardt et al. | |
| 2008/0092061 A1 | 4/2008 | Bankston et al. | |
| 2008/0127726 A1 | 6/2008 | Elkins | |
| 2008/0168826 A1 | 7/2008 | Saidi et al. | |
| 2008/0225273 A1 | 9/2008 | Ershov et al. | |
| 2010/0088031 A1 | 4/2010 | Nielsen et al. | |
| 2010/0091267 A1 | 4/2010 | Wong | |
| 2010/0268480 A1* | 10/2010 | Prince | G01N 1/26 702/24 |
| 2011/0109464 A1 | 5/2011 | Lepley et al. | |
| 2011/0119040 A1 | 5/2011 | McLennan | |
| 2011/0161885 A1 | 6/2011 | Gonia et al. | |
| 2011/0213554 A1* | 9/2011 | Archibald | G01V 9/007 702/6 |
| 2011/0249122 A1 | 10/2011 | Tricoukes et al. | |
| 2011/0251800 A1 | 10/2011 | Wilkins | |
| 2012/0019380 A1 | 1/2012 | Nielsen et al. | |
| 2012/0050143 A1 | 3/2012 | Border et al. | |
| 2012/0072189 A1 | 3/2012 | Bullen et al. | |
| 2012/0113285 A1 | 5/2012 | Baker et al. | |
| 2012/0191349 A1 | 7/2012 | Lenz et al. | |
| 2012/0194541 A1 | 8/2012 | Kim et al. | |
| 2012/0194549 A1 | 8/2012 | Osterhout et al. | |
| 2012/0232915 A1 | 9/2012 | Bromberger | |
| 2013/0179078 A1 | 7/2013 | Griffon | |

OTHER PUBLICATIONS

Turner, Bruce, "Workbook of Atmospheric Dispersion Estimates," p. 1-92. U.S. Environmental Protection Agency, Office of Air Programs. North Carolina, US. Jul. 1971.

Carlbom et al., "Planer Geometric Projections and Viewing Transformations", Computing Surveys, vol. 10:4, p. 465-502, ACM, New York, NY, Dec. 1978.

EPA, "User's Guide for the Industrial Source Complex (ISC3) Dispersion Models, vol. II—Description of Model Algorithms.".p. 1-128. U.S. Environmental Protection Agency. North Carolina, US. Sep. 1995

Rella, U.S. Appl. No. 13/656,123, filed Oct. 19, 2012.
Rella, U.S. Appl. No. 13/656,096, filed Oct. 19, 2012.
Rella, U.S. Appl. No. 13/656,080, filed Oct. 19, 2012.
Tan, U.S. Appl. No. 13/733,864, filed Jan. 3, 2013.
Tan, U.S. Appl. No. 13/733,861, filed Jan. 3, 2013.
Tan, U.S. Appl. No. 13/733,868, filed Jan. 3, 2013.
Tan, U.S. Appl. No. 13/733,857, filed Jan. 3, 2013.
Rella, U.S. Appl. No. 13/913,359, filed Jun. 7, 2013.
Rella, U.S. Appl. No. 13/913,357, filed Jun. 7, 2013.
Keats et al., "Bayesian inference for source determination with applications to a complex urban environment," Atmospheric Environment, vol. 41, Issue 3, pp. 465-479, Jan. 2007.
Rao, Shankar K., "Source estimation methods for atmospheric dispersion," Atmospheric Environment, vol. 41, Issue 33, pp. 6964-6973, Oct. 2007.
Yee et al., "Bayesian inversion of concentration data: Source reconstruction in the adjoint representation of atmospheric diffusion," 4th International Symposium on Computational Wind Engineering, Journal of Wind Engineering and Industrial Aerodynamics, vol. 96, Issues 10-11, pp. 1805-1816, Oct. 2008.
Humphries et al., "Atmospheric Tomography: A Bayesian Inversion Technique for Determining the Rate and Location of Fugitive Emissions," Environmental Science & Technology, 46, 3, pp. 1739-1746, Dec. 12, 2011.
Steele, U.S. Appl. No. 14/139,388, filed Dec. 23, 2013.
Steele, U.S. Appl. No. 14/139,348, filed Dec. 23, 2013.
Prasad Kuldeep R., "Quantification of Methane Emissions From Street Level Data,", http://www.nist.gov/manuscript-publication-search.cfm?pub_id=914433, Abstract #A53E-0213, American Geophysical Union (AGU), Fall Meeting, San Francisco, CA, US, Dec. 9-13, 2013.
Arata C. et al., "Fugitive Methane Source Detection and Discrimination with the Picarro Mobile Methane Investigator," http://adsabs.harvard.edu/abs/2013AGUFM.A53A0150A, Abstract #A53A-0150, American Geophysical Union (AGU), Fall Meeting, San Francisco, CA, US, Dec. 9-13, 2013.
Pavlin G. et al., "Gas Detection and Source Localization: A Bayesian Approach," http://isif.org/fusion/proceedings/Fusion_2011/data/papers/054.pdf, 14th International Conference on Information Fusion, Chicago, Illinois, US, Jul. 2011.
Crosson E. et al., "Quantification of Methane Source Locations and Emissions in AN Urban Setting," http://www.slideserve.com/marly/quantification-of-methane-source-locations-and-emissions-in-an-urban-setting, uploaded on Jul. 31, 2014.
Crosson E. et al., "Quantification of Methane Source Locations and Emissions in AN Urban Setting," http://adsabs.harvard.edu/abs/2011AGUFM.B51Q..04C, American Geophysical Union (AGU), Fall Meeting, San Francisco, CA, US, Dec. 5-9, 2011.
Gas Trak Ltd., "Specializing in: Leak Detection Services for: Natural Gas Pipelines," http://www.slideserve.com/yama/specializing-in-leak-detection-services-for-natural-gas-pipelines, uploaded on Jul. 28, 2013.
Keats, Andrew, "Bayesian inference for source determination in the atmospheric environment," University of Waterloo, Waterloo, Ontario, Canada, 2009, the year of the publication is sufficiently earlier than the effective U.S. filing date and any foreign priority date so that the particular month of publication is not in issue.
USPTO, Office Action dated Jun. 26, 2015 for U.S. Appl. No. 13/733,868, filed Jan. 3, 2013.
USPTO, Office Action dated Jul. 1, 2016 for U.S. Appl. No. 14/139,388, filed Dec. 23, 2013.
USPTO, Office Action dated Nov. 5, 2015 for U.S. Appl. No. 13/733,864, filed Jan. 3, 2013.
USPTO, Office Action dated Nov. 20, 2015 for U.S. Appl. No. 13/733,861, filed Jan. 3, 2013.
USPTO, Notice of Allowance dated Mar. 14, 2016 for U.S. Appl. No. 13/733,868, filed Jan. 3, 2013.
USPTO, Office Action dated May 28, 2015 for U.S. Appl. No. 13/913,357, filed Jun. 7, 2013.
USPTO, Office Action dated May 28, 2015 for U.S. Appl. No. 13/913,359, filed Jun. 7, 2013.
USPTO, Office Action dated Mar. 10, 2016 for U.S. Appl. No. 13/913,357, filed Jun. 7, 2013.
USPTO, Office Action dated Mar. 9, 2016 for U.S. Appl. No. 13/913,359, filed Jun. 7, 2013.
USPTO, Office Action dated Sep. 22, 2016 for U.S. Appl. No. 13/733,861, filed Jan. 3, 2013.

(56) References Cited

OTHER PUBLICATIONS

USPTO, Office Action dated Aug. 25, 2016 for U.S. Appl. No. 13/733,864, filed Jan. 3, 2013.
USPTO, Office Action dated Jun. 28, 2016 for U.S. Appl. No. 14/139,348, filed Dec. 23, 2013.
USPTO, Office Action dated Aug. 28, 2015 for U.S. Appl. No. 13/733,857, filed Jan. 3, 2013.
USPTO, Office Action dated Apr. 20, 2016 for U.S. Appl. No. 13/733,857, filed Jan. 3, 2013.
Wainner et al., High Altitude Natural Gas Leak Detection System, DOE Program Final Report, DOE National Energy Technology Laboratory, Apr. 2007.
Lenz et al., "Flight Testing of an Advanced Airborne Natural Gas Leak Detection System," Final Report, ITT Industries Space Systems LLC, Rochester, NY, Oct. 2005.
Carlbom et al., "Planar Geometric Projections and Viewing Transformations," Computing Surveys, vol. 10: 4, p. 465-502, ACM, New York, NY, Dec. 1978.

* cited by examiner

| Surface wind speed at 10 m (m/s) | Day | | | Night | |
|---|---|---|---|---|---|
| | Incoming Solar radiation | | | Cloud Cover | |
| | Strong | Moderate | Slight | Thinly Overcast (>1/2 cloudy) | Mostly Cloudy |
| < 2 | A | A-B | B | | |
| 2-3 | A-B | B | C | E | F |
| 3-5 | B | B-C | C | D | E |
| 5-6 | C | C-D | D | D | D |
| >6 | C | D | D | D | D |

FIG. 18

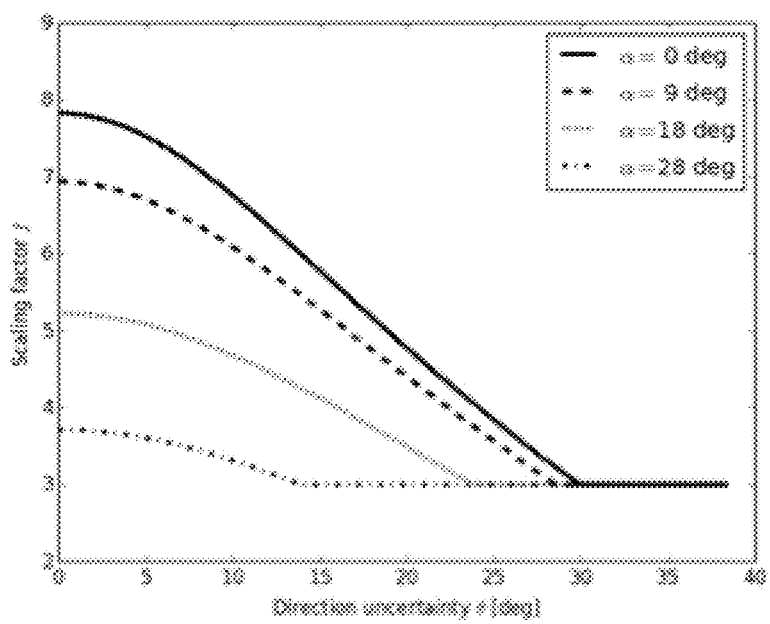
FIG. 23-A
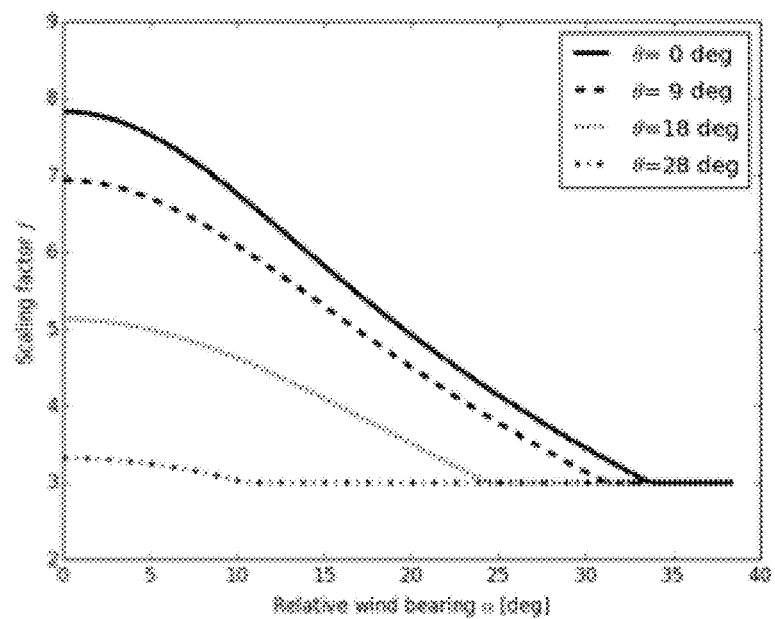
FIG. 23-B

SYSTEMS AND METHODS FOR ASSEMBLING A COLLECTION OF PEAKS CHARACTERIZING A GAS LEAK SOURCE AND SELECTING REPRESENTATIVE PEAKS FOR DISPLAY

BACKGROUND

The invention relates to systems and methods for performing field inspections of natural gas infrastructure to detect gas leaks such as methane gas leaks, and for maintaining and updating geospatial database information related to natural gas infrastructure.

A common means of distributing energy around the world is by the transmission of gas, usually natural gas. In some areas of the world manufactured gasses are also transmitted for use in homes and factories. Gas is typically transmitted through underground pipelines having branches that extend into homes and other buildings for use in providing energy for space and water heating. Many thousands of miles of gas pipeline exist in virtually every major populated area. Since gas is highly combustible, gas leakage is a serious safety concern. Recently, there have been reports of serious fires or explosions caused by leakage of gas in the United States as the pipeline infrastructure becomes older. For this reason, much effort has been made to provide instrumentation for detecting small amounts of gas so that leaks can be located to permit repairs.

One approach to gas leak detection is to mount a gas leak detection instrument on a moving vehicle, e.g., as considered in U.S. Pat. No. 5,946,095. A natural gas detector apparatus is mounted to the vehicle so that the vehicle transports the detector apparatus over an area of interest at exemplary speeds of about 20 miles per hour, sometimes higher or lower. The apparatus is arranged such that natural gas intercepts a beam path and absorbs representative wavelengths of a light beam. A receiver section receives a portion of the light beam onto an electro-optical etalon for detecting the gas.

Although a moving vehicle may cover more ground than a surveyor on foot, there is still the problem of reliably and accurately locating the gas leak source (e.g., a broken pipe) if gas is detected from the vehicle.

SUMMARY

According to one aspect, a computer system comprises at least one processor and associated memory configured to: group a plurality of measured natural gas concentration peaks into a collection assigned to a single natural gas leak, the peaks being defined by natural gas concentration data measured by a mobile measurement device along a survey path, wherein grouping the plurality of peaks is performed according to an inter-peak distance and a representative wind direction characterizing a measurement of the natural gas concentration data; and select for display a subset of representative peaks characterizing the natural gas leak, wherein the collection includes at least one peak not selected as a representative peak for display.

According to another aspect, a non-transitory computer-readable medium encodes instructions which, when executed by a computer system comprising at least one processor, cause the at least one processor to: group a plurality of measured natural gas concentration peaks into a collection assigned to a single natural gas leak, the peaks being defined by natural gas concentration data measured by a mobile measurement device along a survey path, wherein grouping the plurality of peaks is performed according to an inter-peak distance and a representative wind direction characterizing a measurement of the natural gas concentration data; and select for display a subset of representative peaks characterizing the natural gas leak, wherein the collection includes at least one peak not selected as a representative peak for display.

According to another aspect, a method comprises: employing a computer system comprising at least one processor to group a plurality of measured natural gas concentration peaks into a collection assigned to a single natural gas leak, the peaks being defined by natural gas concentration data measured by a mobile measurement device along a survey path, wherein grouping the plurality of peaks is performed according to an inter-peak distance and a representative wind direction characterizing a measurement of the natural gas concentration data; and employing the computer system to select for display a subset of representative peaks characterizing the natural gas leak, wherein the collection includes at least one peak not selected as a representative peak for display.

According to another aspect, a computer system comprises at least one processor and associated memory configured to: group a plurality of measured natural gas concentration peaks into a collection assigned to a single natural gas leak, the measured natural gas concentration peaks being defined by natural gas concentration data measured by a mobile measurement device along a survey path; and select for display a plurality of representative peaks characterizing the natural gas leak, wherein the collection includes at least one peak not selected as a representative peak for display. Selecting for display the plurality of representative peaks comprises: identifying a highest-amplitude peak in the collection, and in response, selecting the highest-amplitude peak for display; identifying a most-upwind peak in the collection, and in response, selecting the most-upwind peak for display; and identifying at least one peak in the collection that meets a predetermined amplitude threshold, and in response, selecting the at least one peak for display.

According to another aspect, a non-transitory computer-readable medium encodes instructions which, when executed by a computer system comprising at least one processor, cause the at least one processor to: group a plurality of measured natural gas concentration peaks into a collection assigned to a single natural gas leak, the measured natural gas concentration peaks being defined by natural gas concentration data measured by a mobile measurement device along a survey path; and select for display a plurality of representative peaks characterizing the natural gas leak, wherein the collection includes at least one peak not selected as a representative peak for display. Selecting for display the plurality of representative peaks comprises: identifying a highest-amplitude peak in the collection, and in response, selecting the highest-amplitude peak for display; identifying a most-upwind peak in the collection, and in response, selecting the most-upwind peak for display; and identifying at least one peak in the collection that meets a predetermined amplitude threshold, and in response, selecting the at least one peak for display.

According to another aspect, a method comprises: employing a computer system comprising at least one processor to group a plurality of measured natural gas concentration peaks into a collection assigned to a single natural gas leak, the measured natural gas concentration peaks being defined by natural gas concentration data measured by a mobile measurement device along a survey path; and employing the computer system to select for display a plurality of representative peaks characterizing the natural gas leak, wherein the collection includes at least one peak not selected as a representative peak for display. Selecting for display the plurality of representative peaks comprises: identifying a highest-amplitude peak in the collection, and in response, selecting the highest-amplitude peak for display; identifying a most-upwind peak in the collection, and in response, selecting the most-upwind peak for display; and identifying at least one peak in the collection that meets a predetermined amplitude threshold, and in response, selecting the at least one peak for display.

BRIEF DESCRIPTION OF THE DRAWINGS

The foregoing aspects and advantages of the present invention will become better understood upon reading the following detailed description and upon reference to the drawings where:

FIG. 18 is a table of dispersion coefficients for various atmospheric conditions according to some embodiments of the present invention.

FIG. 23-A-B show scaling (overlap) factors for downwind peaks as a function of wind variability, and as a function of an angle between a direction of vehicle motion and a wind direction, respectively, computed according to some embodiments of the present invention.

DETAILED DESCRIPTION

Figure 1:
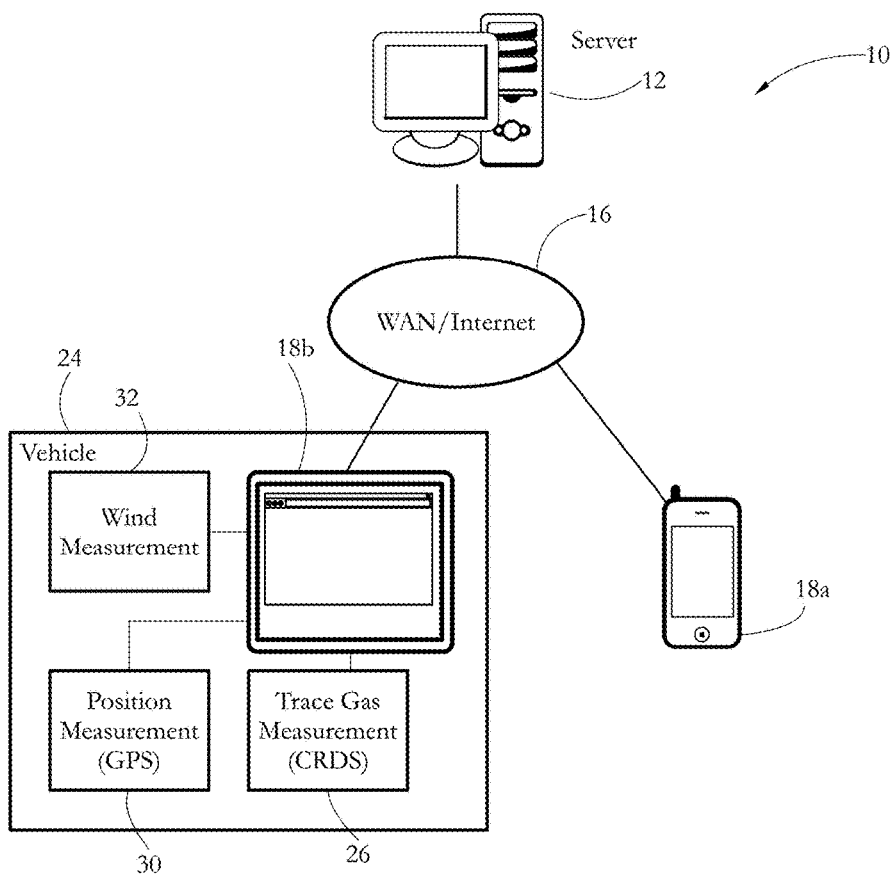
FIG. 1 shows a gas leak detection apparatus according to some embodiments of the present invention.

Apparatus and methods described herein may include or employ one or more interconnected computer systems such as servers, personal computers and/or mobile communication devices, each comprising one or more processors and associated memory, storage, input and display devices. Such computer systems may run software implementing methods described herein when executed on hardware. In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data.

Making a determination or decision according to a parameter encompasses making the determination or decision according to the parameter and optionally according to other data. Unless otherwise specified, an indicator of some quantity/data may be the quantity/data itself, or an indicator different from the quantity/data itself. A synthetic representation refers to an icon or other computer-generated representation, and is distinct from a real-time display of an image captured by a device camera. The term "natural gas" is used below to refer broadly to gases that include methane, whether or not such gasses are fossil fuels pumped out of the ground; for example, in the discussion below, sewers and landfills are described for clarity/simplicity as sources of natural gas, even though the gases generated by a landfill may not be chemically identical to gases extracted from fossil fuel geological deposits. It is understood that recitation of an operation performed on a peak (e.g. grouping, filtering) is not limited to a particular representation of the peak, and may refer to an operation performed on an event characterized by the peak, a search area indicator generated from the peak data, or other data structure representing the peak/event. The terms "natural gas transmission pipeline" and "natural gas distribution pipeline" are both used broadly to refer to pipelines that carry natural gas. The term "wide area network" refers to a network including at least one router. Computer programs described in some embodiments of the present invention may be stand-alone software entities or sub-entities (e.g., subroutines, code objects) of other computer programs. Computer readable media encompass storage (non-transitory) media such as magnetic, optic, and semiconductor media (e.g. hard drives, optical disks, flash memory, DRAM), as well as communications links such as conductive cables and fiber optic links. According to some embodiments, the present invention provides, inter alia, computer systems programmed to perform the methods described herein, as well as computer-readable media encoding instructions to perform the methods described herein.

Finding and grading leaks in a natural gas distribution system using traditional means is slow and costly. There is increasing interest on the part of gas utilities and public utility commissions to improve means to find natural gas leaks quickly and with high detection efficiency. Furthermore, according to a Federal law passed in 2009, utilities in the United States must put in place processes to quantitatively assess risks to their distribution systems. The results of such assessments may then be used, presumably, to prioritize resources and inform other decisions to ensure public safety.

According to one aspect, when an elevated concentration of methane that is consistent with the signature of a gas plume is detected by a measurement system as described below, software reports the amplitude of the background-subtracted maximum concentration and a range of directions toward the likely source of gas emission. Additionally, the software displays a Field of View swath indicating which areas of the survey region have been covered and which have not. A surveyed area output is suitable for incorporation into a risk model, and has to potential to remove much of the human bias that is currently introduced into such models associated with how leak surveys are currently conducted and how survey coverage is accounted for. Reducing such bias allows improving the accuracy of risk calculations and allows for better-informed decision-making.

In particular, vehicle-based natural gas leak detection systems and methods described below allow distinguishing between peaks caused by different leaks, and allow clarifying and simplifying the display of peaks caused by a single, common leak. A collection of measured concentration peaks originating from a common natural gas leak is assembled, and non-representative peaks are filtered out according to wind direction, wind variability and inter-peak distance data. A resulting subset of one or more representative peaks is selected for display to a user. Assigning peaks to a collection may be performed according to a peak overlap condition dependent upon a scaling (overlap) factor which scales the spatial reach of a peak, and according to a wind condition which determines whether a downwind event points toward an upwind event. The scaling factor may depend on wind variability and on an orientation of an inter-peak vector relative to a representative wind direction. Peak filtering is particularly useful in urban environments, where buildings channel gas plumes and one leak may lead to sequential detections of multiple concentration peaks along a path.

Exemplary Hardware and Software Environment

FIG. 1 shows a gas detection and display system 10 according to some embodiments of the present invention. System 10 comprises a service provider server computer system 12 and a set of client computer systems 18*a-b*, all connected through a wide area network 16 such as the Internet. Server computer system 12 may include multiple physical servers of one or more service providers; for example, one service provider may provide map and street view data, while another service provider may provide infrastructure (e.g. plats), and real-time and/or historical gas concentration and wind direction and speed data. Client computer systems 18*a-b* may be portable computing devices such as laptops, smartphones, tablet computers and the like. A vehicle 24 such as an automobile may be used to carry at least some client computer systems (e.g. an exemplary client computer system 18*b*) and associated hardware including a gas analyzer 26, a location/GPS measurement device 30, and a wind measurement device 32. Gas analyzer 26 may be a Picarro analyzer using Wavelength-Scanned Cavity Ring Down Spectroscopy (CRDS), available from Picarro, Inc., Santa Clara, Calif. Such analyzers may be capable of detecting trace amounts of gases such as methane, acetylene, carbon monoxide, carbon dioxide, hydrogen sulfide, and/or water. In particular applications suited for detection of natural gas leaks, a Picarro G2203 analyzer capable of detecting methane concentration variations of 3 ppb may be used. Wind measurement device 32 may include a wind anemometer and a wind direction detector (e.g. wind vane). GPS measurement device 30 may be a stand-alone device or a device built into client computer system 18*b*.

Figure 2:
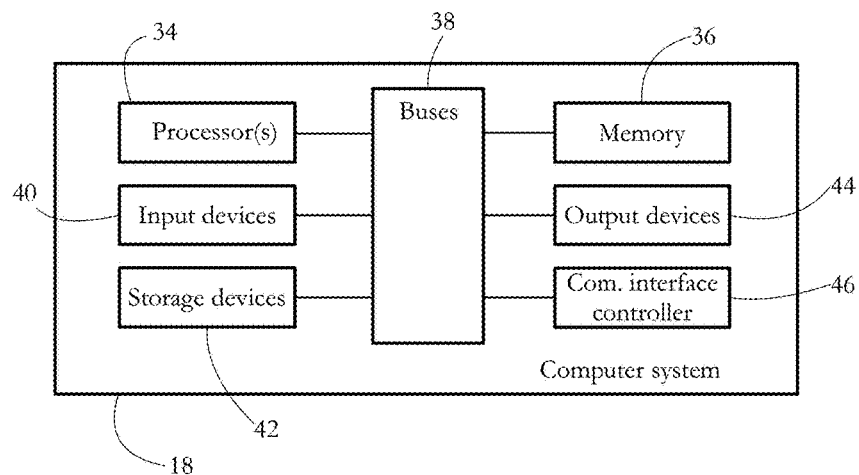
FIG. 2 illustrates hardware components of a computer system according to some embodiments of the present invention.

Each computer system 18 comprises a plurality of hardware components, schematically illustrated in FIG. 2. Such computer systems may be devices capable of web browsing and thus access to remotely-hosted protected websites, such as desktop, laptop, tablet computer devices, or mobile phones such as smartphones. In some embodiments, computer system 18 comprises one or more processors 34, a memory unit 36, a set of input devices 40, a set of output devices 44, a set of storage devices 42, and a communication interface controller 46, all connected by a set of buses 38. In some embodiments, processor 34 comprises a physical device (e.g. multi-core integrated circuit) configured to execute computational and/or logical operations with a set of signals and/or data. In some embodiments, such logical operations are delivered to processor 34 in the form of a sequence of processor instructions (e.g. machine code or other type of software). Memory unit 36 may comprise random-access memory (RAM) storing instructions and operands accessed and/or generated by processor 34. Input devices 40 may include touch-sensitive interfaces, computer keyboards and mice, among others, allowing a user to introduce data and/or instructions into system 18. Output devices 44 may include display devices such as monitors. In some embodiments, input devices 40 and output devices 44 may share a common piece of hardware, as in the case of touch-screen devices. Storage devices 42 include computer-readable media enabling the storage, reading, and writing of software instructions and/or data. Exemplary storage devices 42 include magnetic and optical disks and flash memory devices, as well as removable media such as CD and/or DVD disks and drives. Communication interface controller 46 enables system 18 to connect to a computer network and/or to other machines/computer systems. Typical communication interface controllers 46 include network adapters. Buses 38 collectively represent the plurality of system, peripheral, and chipset buses, and/or all other circuitry enabling the inter-communication of devices 34-46 of computer system 18.

Figure 3:
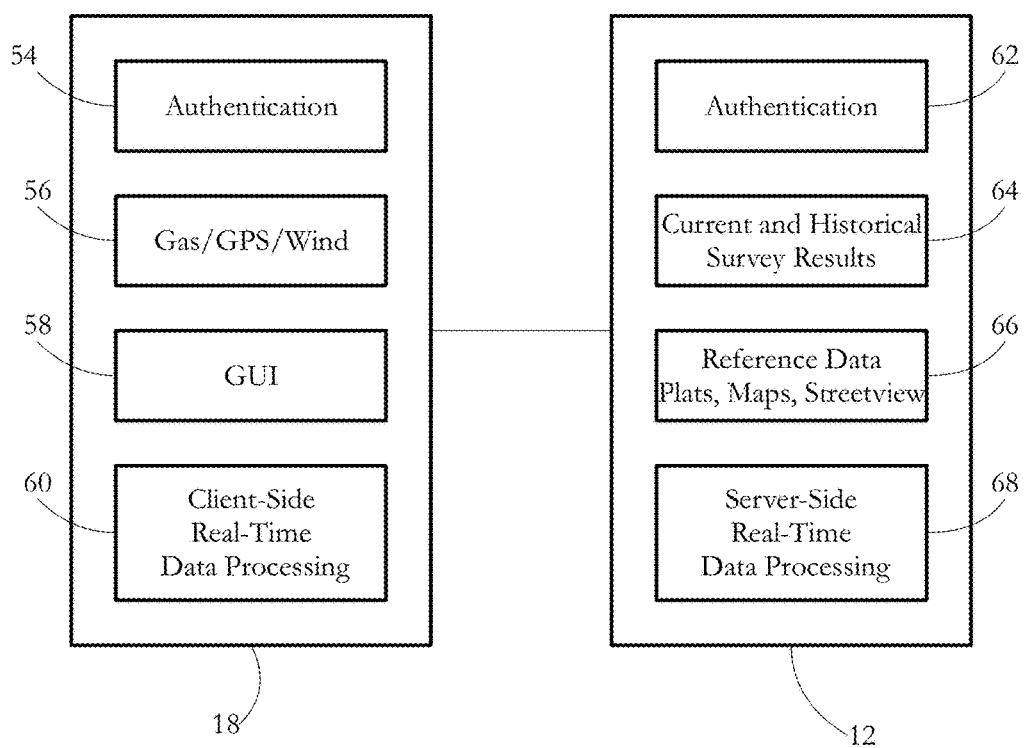
FIG. 3 shows a number of application or modules running on a client computer system and a corresponding server computer system according to some embodiments of the present invention.

FIG. 3 shows a number of applications or modules running on an exemplary client computer system 18 and corresponding server computer system 12. Authentication applications 54, 62 are used to establish secure communications between computer systems 12, 18, allowing client computer system 18 selective access to the data of a particular customer or user account. A client data collection module 56 collects real-time gas concentration, location data such as global positioning system (GPS) data, as well as wind speed and wind direction data. A client GUI module 58 is used to receive user input and display results as described herein. A client-side real-time data processing module 60 is used to perform at least some of the data processing described herein to generate survey results from input data. Other data processing may be performed by a server-side data processing module 68. Server computer system 12 also maintains one or more application modules and/or associated data structures storing current and past survey results 64, as well as application modules and/or data structures storing reference data 66 such as plats indicating the geographic locations of natural gas pipelines, map data, and street view images.

Exemplary GUI Design

Figure 4:
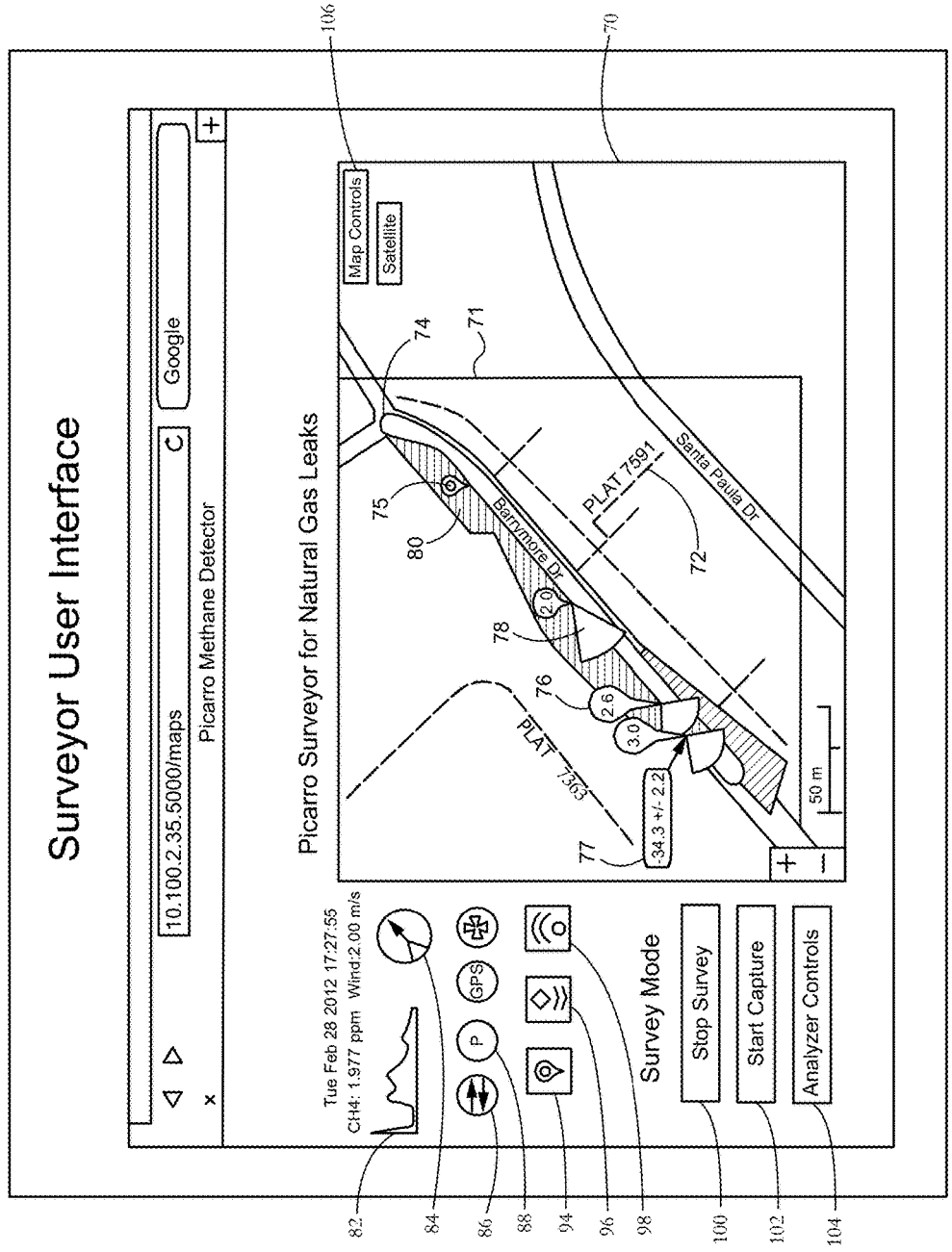
FIG. 4 is a schematic drawing of a screen shot on a graphical user interface displaying survey results on a street map according to some embodiments of the present invention.

FIG. 4 is a schematic drawing of a screen shot on a graphical user interface, displaying survey results on a street map 70 according to some embodiments of the present invention. The GUI screenshots may be displayed on a client device in the vehicle, which may be connected to a server as described above. The illustrated screenshots show both exemplary user input, which may be used to control system operation, and exemplary real-time displays of collected/processed data. In the example, the display includes the geo-referenced street map 70 showing plat lines 72. The plat lines 72 are preferably derived from gas company records. An active pipeline plat boundary 71 may also be displayed on the map 70. A user-selectable button 96 may be selected to overlay a selected pipeline plat on the map 70. Superimposed on the map 70 are one or more lines (preferably in a distinguishing color not shown in patent drawings) indicating the path 74 driven by the vehicle with the mobile gas measurement device on one or more gas survey routes. In this example, the path 74 shows the vehicle U-turned at the Y-shaped intersection. Optionally, a current location icon 75 may be overlaid on the map 70 to indicate the current surveyor location, e.g., the position of the vehicle with a gas measurement device and wind measurement device. A user-selectable button 94 may be selected to center the map 70 by current surveyor location. Also provided is a user-selectable start button 102 and stop button 100 to start/stop capturing gas for analysis. An analyzer control button 104 is user-selectable to control analyzer operations (e.g., shut down, start new trace, run isotopic analysis, etc.).

Peak markers 76 show the locations along the path 74 where peaks in the gas concentration measurements, which satisfy the conditions for being likely gas emission indications, were identified. The colors of the peak markers 76 may be used to distinguish data collected on different runs. The annotations within the peak markers 76 show the peak concentration of methane at the locations of those measurement points (e.g., 3.0, 2.6, and 2.0 parts per million). An isotopic ratio marker 77 may be overlaid on the map 70 to indicate isotopic ratio analysis output and tolerance (e.g., −34.3+/−2.2). Also displayed on the map 70 are search area indicators 78, preferably shown as a sector of a circle having a distinguishing color. Each of the search area indicators 78 indicates a search area suspected to have a gas emission (e.g. leak) source. The opening angle of the search area indicator 78 depicts the variability in the wind direction. The orientation of the axis of the search area indicator 78 (preferably an axis of symmetry) indicates the likely direction to the potential gas leak source. Also displayed on the map 70 are one or more surveyed area indicators 80 (shown as hatched regions in FIG. 4) that indicate a survey area for a potential gas leak source. The surveyed area indicator 80 adjoins path 74 and extends in a substantially upwind direction from the path 74. The survey area marked by each indicator 80 is preferably displayed as a colored swath overlaid or superimposed on the map 70. For example, the colored swaths may be displayed in orange and green for two runs. In preferred embodiments, the parameters of the search area indicators 78 and the survey area indicators 80 (described in greater detail below) are generated according to measurements of wind direction and speed, the velocity of the vehicle, and optionally the prevailing atmospheric stability conditions.

Referring still to FIG. 4, the surveyor user interface may also include a real-time CH4 concentration reading 82. A wind indicator symbol 84 may display real-time wind information, which may be corrected for the velocity vector of the vehicle to represent the true wind rather than the apparent wind when the vehicle is in motion. Average wind direction is indicated by the direction of the arrow of the wind indicator symbol 84, while wind direction variability is indicated by the degree of open angle of the wedge extending from the bottom of the arrow. Wind speed is indicated by the length of the arrow in the wind indicator symbol 84. An internet connection indicator 98 blinks when the internet connection is good. A data transfer status button 86 is user-selectable to display data transfer status (e.g., data transfer successful, intermittent data transfer, or data transfer failed). An analyzer status button 88 is user-selectable to display current analyzer status such as cavity pressure, cavity temperature, and warm box temperature. A map control button 106 is user-selectable to open a map controls window with user-selectable layer options, discussed below with reference to FIG. 7.

Figure 5:
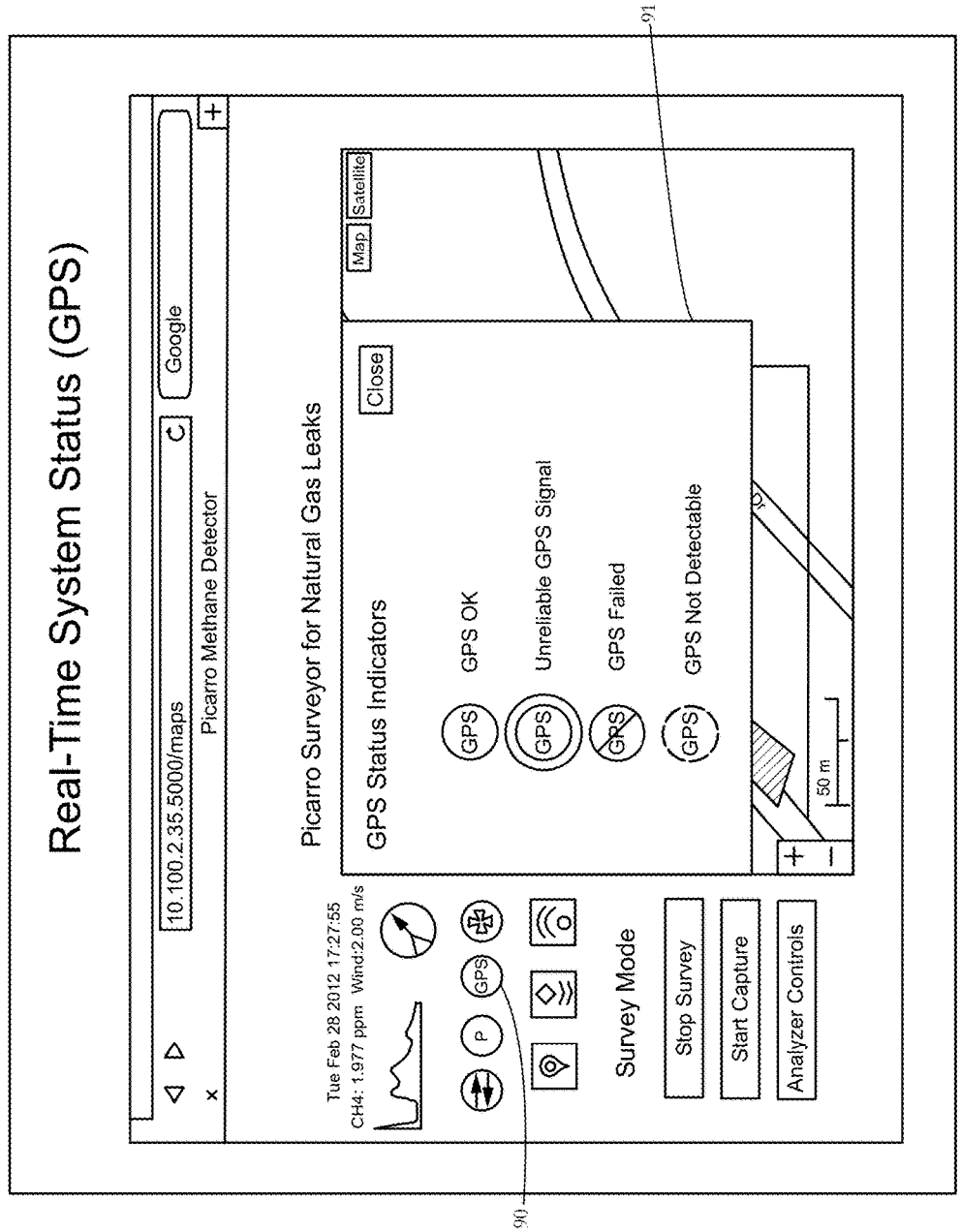
FIG. 5 is a schematic drawing of a screen shot on a graphical user interface with GPS indicators according to some embodiments of the present invention.

FIG. 5 is a schematic drawing of a screen shot on the graphical user interface, displaying a GPS status window 91, according to some embodiments of the present invention. A user-selectable GPS status button 90 may be selected to open the GPS status window 91. The GPS status window 91 preferably includes indicators of the current GPS status, such as "GPS OK", "Unreliable GPS signal", "GPS Failed", or "GPS Not Detectable".

Figure 6:
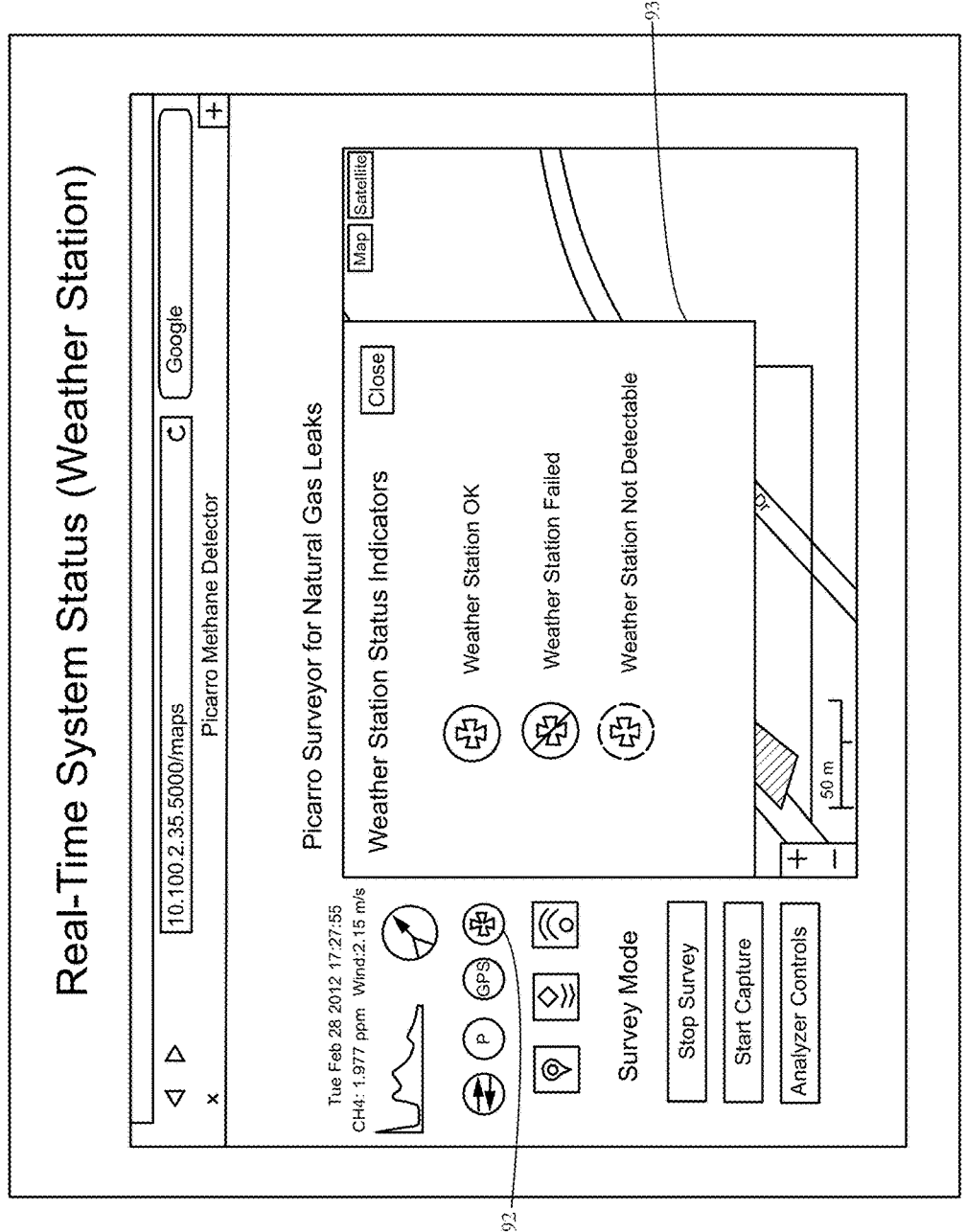
FIG. 6 is a schematic drawing of a screen shot on a graphical user interface with weather station status indicators according to some embodiments of the present invention.

FIG. 6 is a schematic drawing of a screen shot on the graphical user interface, displaying a weather station status window 93, according to some embodiments of the present invention. A user-selectable weather station status button 92 may be selected to open the weather station status window 93. The weather station status window 93 preferably includes indicators of the current weather station status, such as "Weather Station OK", "Weather Station Failed", or "Weather Station Not Detectable". Weather station data are preferably received in real-time and may include wind data and atmospheric stability conditions data relevant to the area being surveyed.

Figure 7:
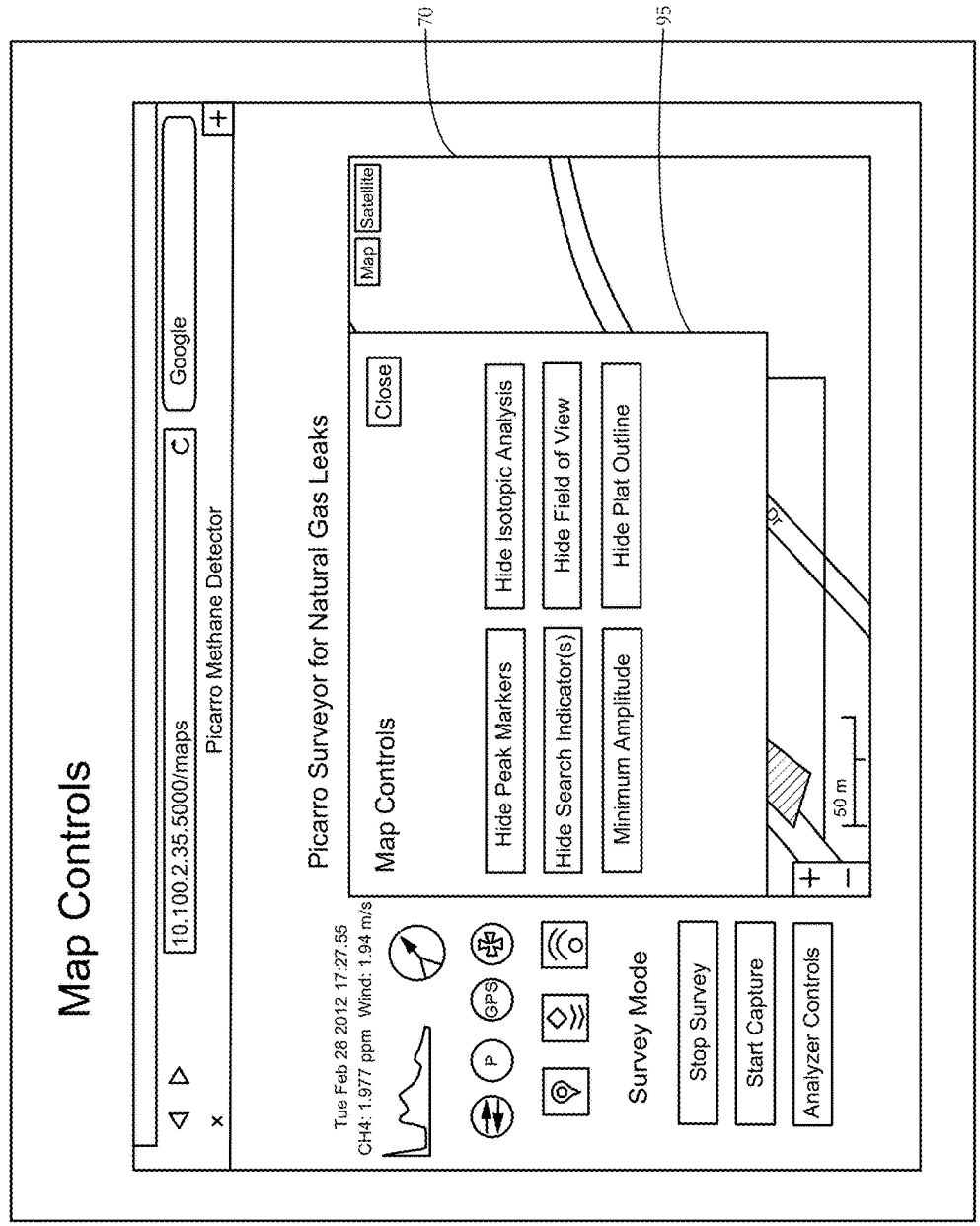
FIG. 7 is a schematic drawing of a screen shot on a graphical user interface with map controls according to some embodiments of the present invention.

FIG. 7 is a schematic drawing of a screen shot on the graphical user interface, displaying a map control window 95. Various elements displayed on the map 70 are regarded as layers which may be turned on or off. In this example, map controls window 95 includes six user-selectable buttons named "Hide Peak Markers", "Hide Search Area Indicators", "Minimum Amplitude", "Hide Isotopic Analysis", "Hide Field of View", and "Hide Plat Outline". The "Hide Peak Markers" button may be selected so that the markers indicating peak gas concentration measurements are not displayed on the map 70. The "Hide Search Area Indicators" button may be selected so that the search area indicators are not displayed on the map 70. The "Minimum Amplitude" button may be selected so that gas concentration peaks not meeting a minimum amplitude requirement are not displayed on the map 70. The "Hide Isotopic Analysis" button may be selected so that isotopic ratio analysis information is not displayed on the map 70 next to the peak markers. The "Hide Field of View" button may be selected so that the survey area indicator(s) are not displayed on the map 70. The "Hide Plat Outline" button may be selected so that the plat lines are not displayed on the map 70.

Exemplary Gas Emission Data Collection and Analysis

Figure 8:
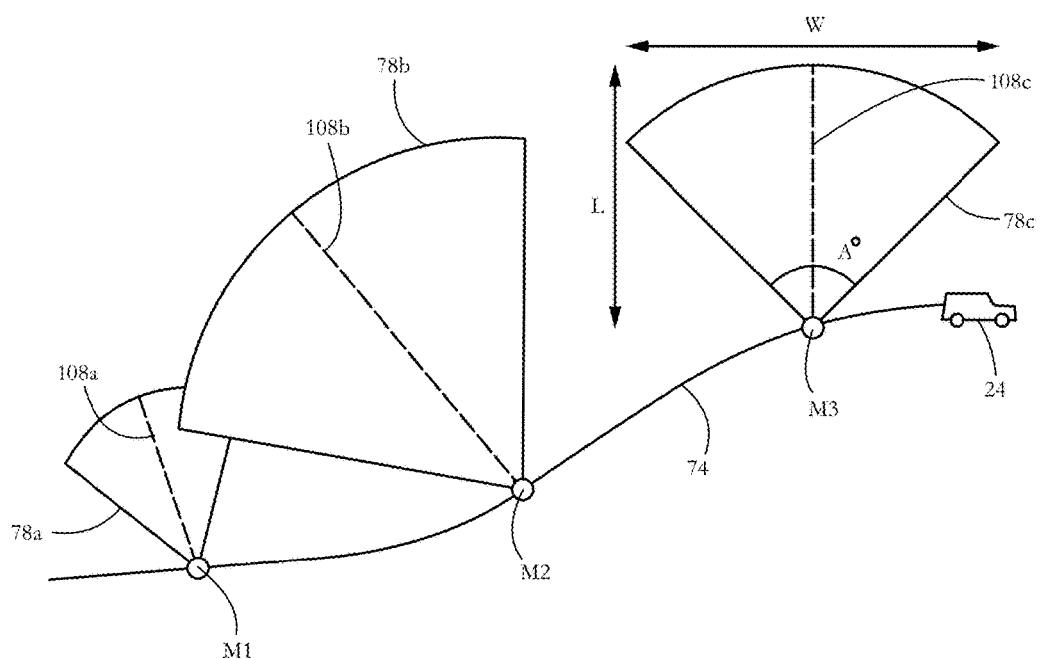
FIG. 8 is a schematic diagram of three search area indicators according to some embodiments of the present invention.

FIG. 8 is a schematic diagram of three search area indicators 78a, 78b, and 78c according to some embodiments of the present invention. Each of the search area indicators 78a, 78b, and 78c has a respective axis 108a, 108b, and 108c indicating a representative wind direction relative to a geo-referenced location of a corresponding gas concentration measurement point M1, M2, and M3. The gas concentration measurement points M1, M2, and M3 are positioned along the path 74 traveled by the vehicle 24 that carries a GPS device, a mobile gas measurement device, and wind measurement device for taking wind direction measurements and wind speed measurements. Each of the search area indicators, such as the search area indicator 78c, preferably has a width W relative to its axis 108c. The width W is indicative of a wind direction variability associated with wind direction measurements in the area of the gas concentration measurement point M3. In preferred embodiments, the width W is indicative of a variance or standard deviation of the wind direction measurements. Also in preferred embodiments, the search area indicator 78c has the shape of a sector of a circle, with the center of the circle positioned on the map at the location of the gas concentration measurement point M3. Most preferably, the angle A subtended by the sector of the circle is proportional to a standard deviation of the wind direction measurements taken at or nearby the measurement point M3. For example, the angle A may be set to a value that is twice the angular standard deviation of the wind direction measurements. It is not necessary to display the gas concentration measurement points M1, M2, and M3 on the map along with the search area indicators 78a, 78b, and 78c. As previously shown in FIGS. 4 and 7, the measurement points and associated gas concentration measurements are preferably map layer options for an end-user that may be turned on or off.

Referring again to FIG. 8, the axis 108c of the search area indicator 78c is preferably an axis of symmetry and points in a representative wind direction relative to the gas concentration measurement point M3. The representative wind direction may be a mean, median or mode of the wind direction measurements taken at or nearby the measurement point M3, and indicates the likely direction to a potential gas leak source. The wind direction measurements may be taken from the vehicle 24 as it moves and converted to wind direction values relative to the ground (e.g., by subtracting or correcting for the velocity vector of the vehicle). In some embodiments, the axis 108c has a length L indicative of a maximum detection distance value representative of an estimated maximum distance from a potential gas leak source at which a gas leak from the source can be detected. For example, the length may be proportional to the maximum detection distance value, or proportional to a monotonically increasing function of the maximum detection distance value, such that longer maximum detection distance values are represented by longer axis lengths. In preferred embodiments, the maximum detection distance value and corresponding length L are determined according to data representative of wind speed in the search area. In some embodiments, the maximum detection distance value and the corresponding length L are determined according to data representative of atmospheric stability conditions in the search area. Each of the search area indicators 78a, 78b, and 78c may thus provide a visual indication of a likely direction and estimated distance to a potential gas leak source. Although a sector of a circle is the presently preferred shape for a search area indicator, alternative shapes for a search area indicator include, but are not limited to, a triangle, a trapezoid, or a wedge.

Figure 9:
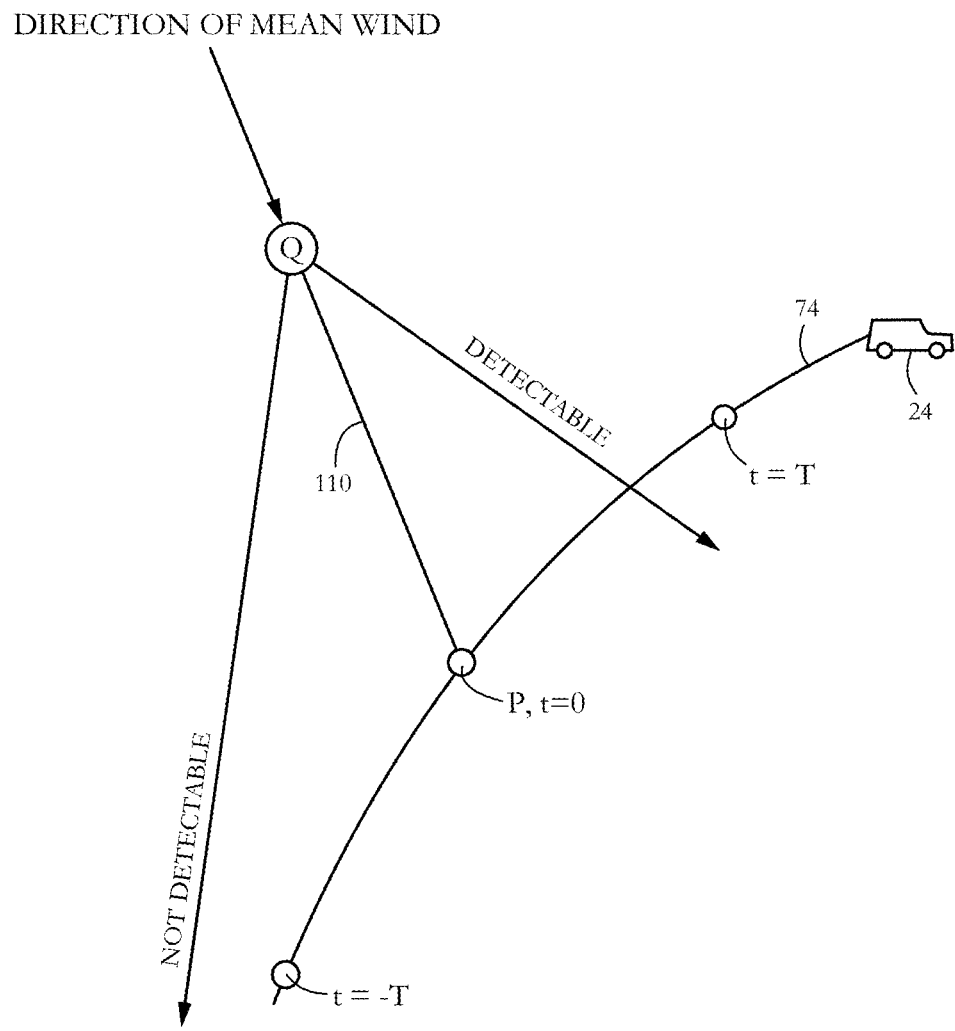
FIG. 9 is a schematic diagram illustrating wind lines relative to the path of a mobile gas measurement device for detecting or not detecting a gas leak from a potential gas leak source according to some embodiments of the present invention.

FIG. 9 is a schematic diagram illustrating an example of detecting or not detecting a gas leak from a potential gas leak source, according to some embodiments of the present invention. An indicator of a surveyed area (also sometimes referred to as a "field of view" below) provides an indication of how well the measurement process has surveyed the area around the path 74 traveled by the vehicle 24 that carries a GPS device, a mobile gas measurement device, and wind measurement device. The surveyed area indicator is designed such that if a potential gas emission (e.g. leak) source is located in the survey area and has a rate of emission meeting a minimum emission rate condition, then an estimated probability of detection of a gas emission from the potential gas emission source at one or more measurement points P along the path 74 satisfies a probability condition.

Whether or not a potential gas emission source of a given strength is detectable by a gas measurement device of a given sensitivity depends on the separation distance of the source from the gas measurement device and on whether the wind is sufficient to transport gas from the gas emission source to the gas measurement device at some point along the path 74. In some embodiments, a physical model is employed that relates the measured gas concentration peak at the location of the vehicle 24 (in ppm, for example) to the emission rate of the potential gas emission source (in g/sec, for example) and the distance between the source and the detection point.

There are multiple possible models that describe the propagation of a gas emission as a plume through the atmosphere. One well-validated physical model for a plume (Gifford, F. A., 1959. "Statistical properties of a fluctuating plume dispersion model". Adv. Geophys, 6, 117-137) is to model the plume as a Gaussian distribution in the spatial dimensions transverse to the wind direction. For a ground level source, the concentration c (x, y, z) at a distance x downwind, y crosswind, and at a height z from a gas emission source of strength Q located on the ground is then given by Equation (1):

$$C(x, y, z) = \frac{Q}{\pi v \sigma_y \sigma_z} e^{-y^2/2\sigma_y^2 - z^2/2\sigma_z^2} \quad [1]$$

where v is the speed of the wind, and the plume dispersion half-widths $\sigma_y$ and $\sigma_z$ depend on x via functions that are empirically determined for various atmospheric stability conditions.

If we consider the plume center, where y=z=0, the concentration at the center is given by Equation (2):

$$C_{peak} = \frac{Q}{\pi v \sigma_y \sigma_z} \quad [2]$$

The dimensions of the Gaussian distribution horizontally and vertically, half-widths $\sigma_y$ and $\sigma_z$, increase with increasing distance from the source. The amount they increase can be estimated from measurements of wind speed, solar irradiation, ground albedo, humidity, and terrain and obstacles, all of which influence the turbulent mixing of the atmosphere. However, if one is willing to tolerate somewhat more uncertainty in the distance estimation, the turbulent mixing of the atmosphere can be estimated simply from the wind speed, the time of day, and the degree of cloudiness, all of which are parameters that are available either on the vehicle 24 or from public weather databases in real time. Using these available data, estimates of the Gaussian width parameters can be estimated using the Pasquill-Gifford-Turner turbulence typing scheme (Turner, D. B. (1970). "Workbook of atmospheric dispersion estimates". US Department of Health, Education, and Welfare, National Center for Air Pollution Control), or modified versions of this scheme.

For a given sensitivity of the gas measurement device, there is a minimum concentration which may be detected. Given a gas emission source of strength greater than or equal to the minimum concentration, the source will be detected if it is closer than an estimated maximum distance $X_{max}$, where this is the distance such that $\sigma_y \sigma_z = Q/(\pi v c)$. If the wind is blowing gas directly from the gas emission source to the gas measurement device, the estimated maximum distance $X_{max}$ is the distance beyond which the source may be missed. This estimated maximum detection distance may depend upon atmospheric stability conditions as well as wind speed. The formula diverges to infinity when the wind speed is very small, so in some embodiments it may be advisable to set a lower limit (e.g., 0.5 m/s) for this quantity.

The minimum emission rate $Q_{min}$ is determined by the requirements of the application. For natural gas distribution systems, a minimum leak rate of 0.5 scfh (standard cubic feet per hour) may be used; below this level, the leak may be considered unimportant. Other minimum leak rates (e.g. 0.1 scfh, 1 scfh, or other values within or outside this range) may be used for natural gas or other leak detection applications. The minimum detection limit of the plume $C_{min}$ is given either by the gas detection instrument technology itself, or by the spatial variability of methane in the atmosphere when emissions are not present. A typical value for $C_{min}$ is 30 ppb (parts-per-billion) above the background level (typically 1,800 ppb). Given these two values for $Q_{min}$ and $C_{min}$, and by predicting $\sigma_y$ and $\sigma_z$ given atmospheric measurements (or with specific assumptions about the state of the atmosphere, such as the stability class), one may then determine the estimated maximum detection distance $X_{max}$ by determining the value for $X_{max}$ that satisfies the following equality, Equation (3):

$$C_{min} = \frac{Q_{min}}{\pi v \sigma_y \sigma_z}. \quad [3]$$

In some embodiments the relationship between $\sigma_y$ and $\sigma_z$ and $X_{max}$ is provided by a functional relationship, a lookup table, or similar method. Because $\sigma_y$ and $\sigma_z$ are monotonically increasing functions of $X_{max}$, a unique value can be determined from this process. For example, one useful functional form is a simple power law, where the coefficients a, b, c, and d depend on atmospheric conditions: $\sigma_y = ax^b$; $\sigma_z = cx^d$.

In some embodiments, the concentration C measured close to the ground of a Gaussian plume due to a gas leak source on the ground depends on the rate of emission Q of the source, the distance x between the source and the gas measurement device, and the speed of the wind blowing from the source to the gas measurement device, in accordance with an expression of the form (Equation 4):

$$C = \frac{Q}{\pi v \sigma_y(x) \sigma_z(x)} \quad [4]$$

The expressions for $\sigma_y(x)$ and $\sigma_z(x)$ depend on the stability class of the atmosphere at the time of measurement. In some embodiments, the stability class of the atmosphere is inferred from the answers to a set of questions given to the operator, or from instruments of the vehicle, or from data received from public weather databases. As shown in the table of FIG. 18, coefficients A, B, C, D, E and F may depend on surface wind speed and atmospheric conditions such as day or night, incoming solar radiation, and cloud cover. Mathematical forms for $\sigma_y(x)$ and $\sigma_z(x)$ are documented in Section 1.1.5 of the User's Guide for Industrial Source Complex (ISC3), Dispersion Models Vol. 2 (US Environmental Protection Agency document EPA-454/B955-003b September 1995). Given the sensitivity of the gas measurement device and the rate of emission of the smallest potential gas leak source of interest, equation (4) may be solved to find the estimated maximum distance $X_{max}$ beyond which a potential gas leak source may be missed by the gas measurement device.

Figure 16:
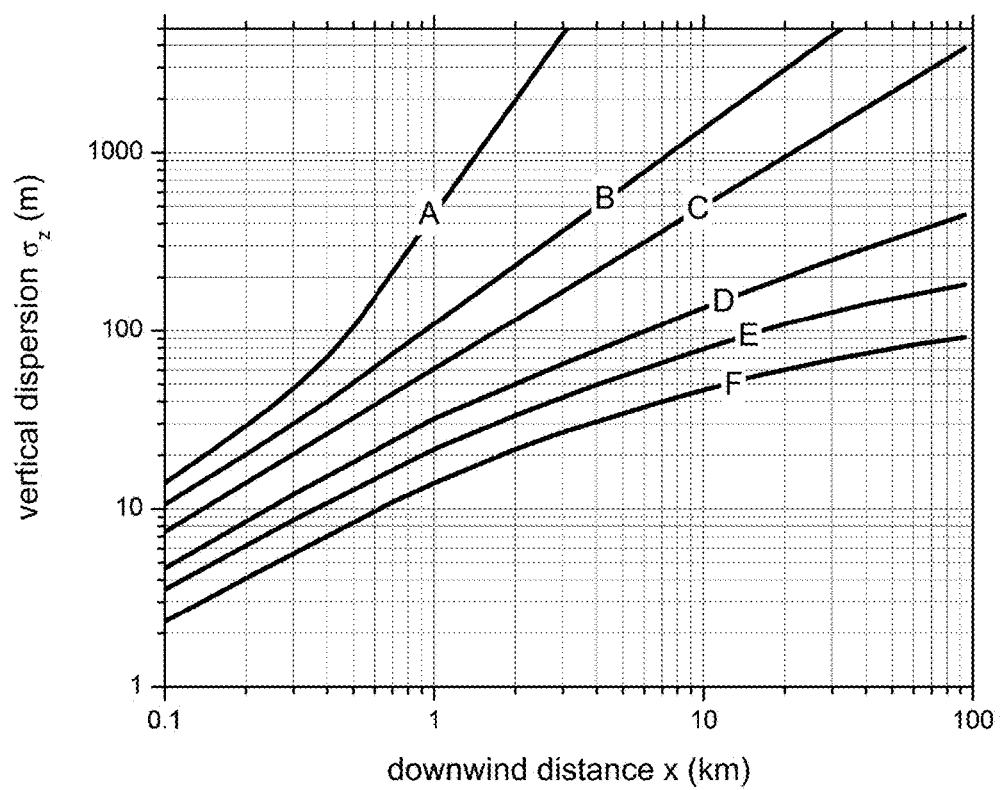
FIG. 16 is a graph of vertical dispersion coefficients of a gas plume as a function of downwind distance from a gas leak source according to some embodiments of the present invention.
Figure 17:
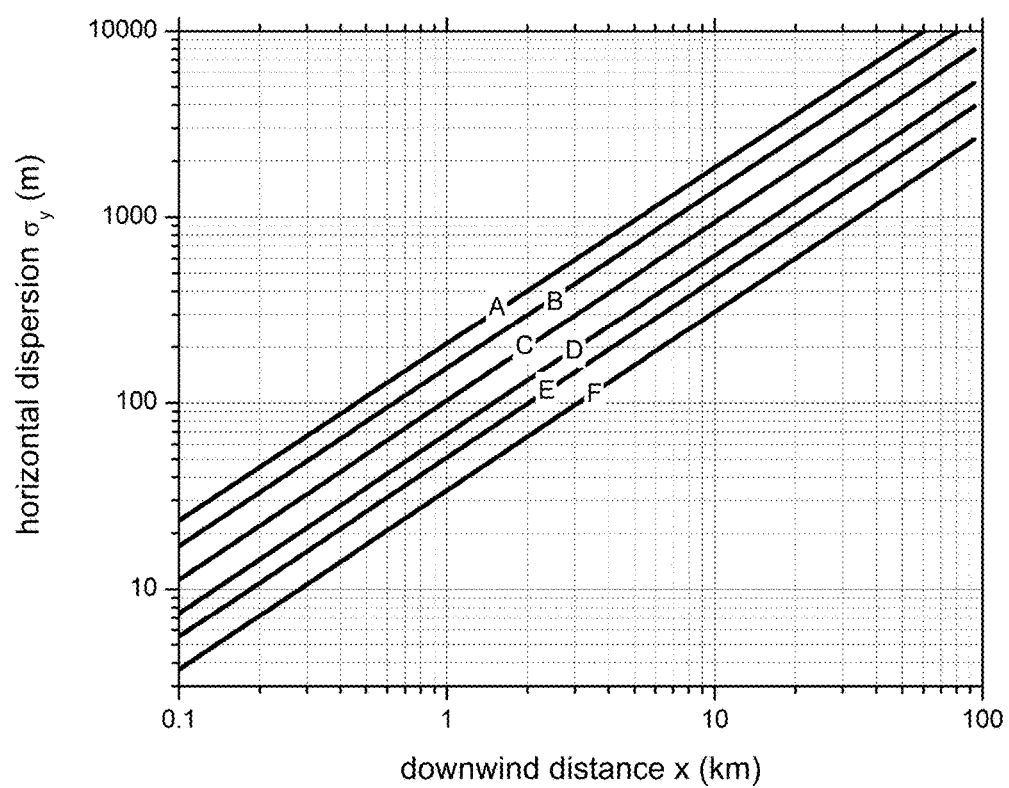
FIG. 17 is a graph of crosswind dispersion coefficients of a gas plume as a function of downwind distance from a gas leak source according to some embodiments of the present invention.

FIG. 16 is a graph of vertical $\sigma_z(x)$ dispersion coefficients of a gas plume as a function of downwind distance from a gas leak source according to some embodiments of the present invention. FIG. 17 is a graph of crosswind $\sigma_y(x)$ dispersion coefficients of a gas plume as a function of downwind distance from a gas leak source according to some embodiments of the present invention. The graphs are from from de Nevers, 2000, Air Pollution Control Engineering, The McGraw-Hill Companies, Inc. The dispersion coefficients are functions of downwind distance x. In this example, dispersion coefficients are calculated based on atmospheric stability. The table of FIG. 18 gives the atmospheric stability class as a function of wind speed, day or night, cloud cover, and solar radiation. In some embodiments, the dispersion coefficients and/or the estimated maximum distance $X_{max}$ may depend upon an urban or rural environment for the gas concentration measurements and plume dispersion. For example, the estimated maximum distance $X_{max}$ may be less in an urban environment with buildings or other structures than in a rural environment.

The actual distance at which a gas emission source may be detected is reduced if there is some variability or uncertainty in the direction of the wind. This is because there is a probability that the wind blows gas in a direction such that it does not intercept the path 74 of the vehicle 24 (FIG. 9). In practice this uncertainty is usually larger than the intrinsic angular uncertainty $\sigma_y/x$ implied by the Gaussian plume model. In order to determine the effective survey area of the mobile gas measurement device, assume for this example that the wind speed remains approximately constant within a time interval $-T<t<T$ bounding the time $t=0$ at which the vehicle 24 passes through a particular point P on the path 74, but that the wind direction (angle) is distributed as a Gaussian with a known mean and standard deviation.

As shown in FIG. 9, we consider the line 110 through the measurement point P pointing toward the direction of the mean wind, and whether a candidate point Q on this line qualifies to be within the boundary of the survey area (i.e., within the field of view of the mobile gas measurement device of the vehicle 24). We also consider drawing a sample from the distribution of wind directions and drawing a line through the candidate point Q in this direction. If this line intersects the path 74 of the vehicle 24 within the time interval $-T<t<T$, and the distance from the candidate point Q to the point of intersection with the path 74 is less than or equal to the estimated maximum distance $X_{max}$, then this is regarded as detectable by the mobile gas measurement device since the potential gas emission source at the candidate point Q would have been detected along the path 74. The quantity T sets the time interval during which it is expected to detect the gas coming from the candidate point Q at measurement point P. Theoretically, the time interval can be large, but it may not be reasonable to assume that the wind statistics remain unchanged for an extended period of time. In some embodiments, the wind direction measurements are taken during a time interval less than or equal to about 2 minutes, during which time interval a gas concentration is measured at the gas concentration measurement point P. More preferably, the time interval is in the range of 10 to 20 seconds.

Figure 10:
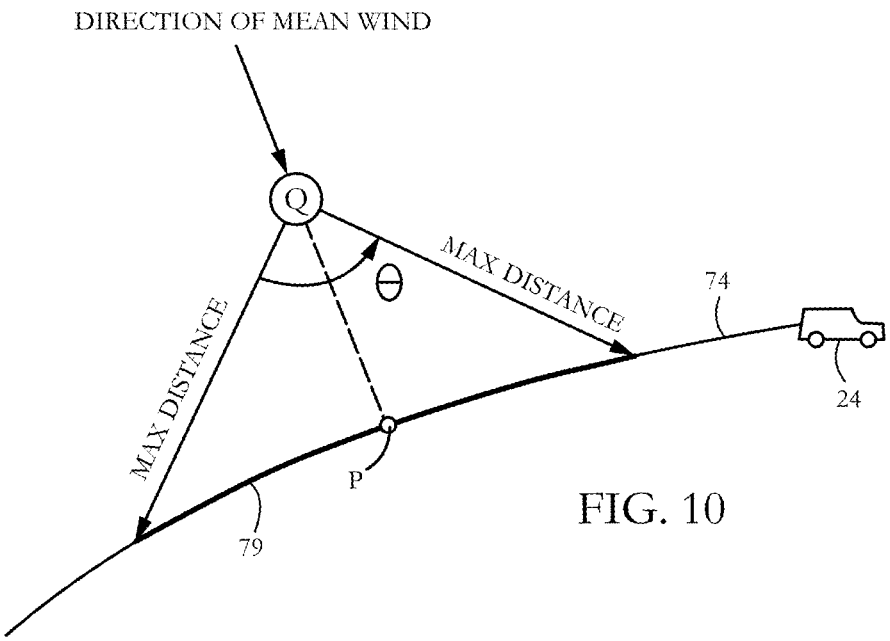
FIG. 10 is a schematic diagram of wind direction and a path of a mobile gas measurement device used to estimate a probability of detection of a gas leak from a potential gas leak source at one or more measurement points along the path according to some embodiments of the present invention.

FIG. 10 is a schematic diagram showing the estimation of a probability of detection at the measurement point P of a gas emission from a potential gas emission source at the candidate point Q, according to some embodiments of the present invention. The probability of detection at measurement point P is estimated according to an angle $\theta$ subtended by a segment 79 of the path 74 relative to the candidate point Q for the potential gas emission source. The path segment 79 is positioned within a distance of the candidate point Q that is less than or equal to the estimated maximum distance $X_{max}$. The probability of detection is preferably estimated according to a cumulative probability of wind directions with respect to the subtended angle $\theta$. The cumulative probability of wind directions may be determined according to a representative wind direction (e.g., a mean, median, or mode of the wind direction measurements) and a wind direction variability (e.g., variance or standard deviation) calculated from the wind direction measurements.

The candidate point Q is deemed to be within the boundary of the survey area if the probability of successful detection of a potential gas leak source at the candidate point Q, over the distribution of wind directions, satisfies a probability condition. In some embodiments, the probability condition to be satisfied is an estimated probability of successful detection greater than or equal to a threshold value, typically set at 70%. In general, as the candidate point Q is moved a farther distance from the gas concentration measurement point P, the range of successful angles becomes smaller and the probability of success decreases, reaching a probability threshold at the boundary of the territory deemed to be within the survey area.

Figure 11:
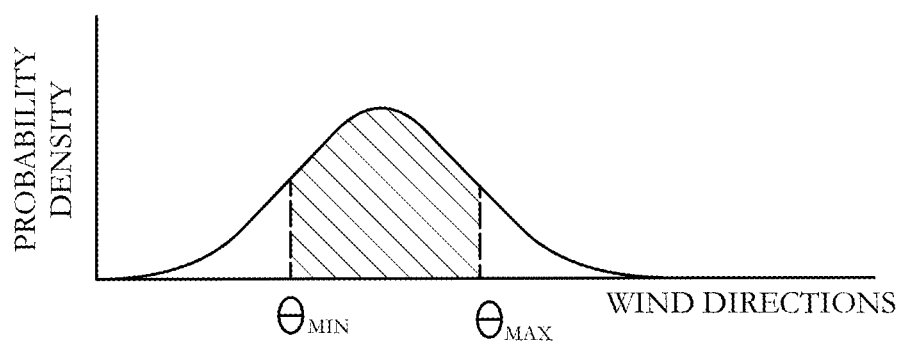
FIG. 11 is a graph of probability density vs. wind directions for estimating a probability of detection of a gas leak from a potential gas leak source according to some embodiments of the present invention.

FIG. 11 is a graph of probability density vs. wind directions for estimating a probability of detection of a gas leak from a potential gas leak source, according to some embodiments of the present invention. The area under the curve spans a range of possible angles $\theta$ for the successful detection of a potential gas leak from a candidate point. The probability density may be generated as a Gaussian or similar distribution from the calculated mean and standard deviation of the wind direction measurements in the area of the gas concentration measurement point P, FIG. 10. If the angle $\theta$ subtended by the path segment 79 relative to the candidate point Q encompasses a cumulative probability that is greater than equal to a threshold percentage (e.g., 70%, although the percentage may be adjusted to other values such as 50%, 60%, 67%, 75%, 80%, or 90% in some embodiments), and if the distance from the candidate point Q to the measurement point P is less than the estimated maximum distance $X_{max}$, then the candidate point Q is deemed to be within the survey area.

The above process is repeated as different measurement points along the path 74 are chosen and different candidate points are evaluated for the probability of successful detection of a potential gas leak source. The cumulative distribution of the wind direction function together with a root finding algorithm are useful for efficiently determining the boundary of the survey area. For example, referring again to FIG. 10, the root finding algorithm may consider candidate points along the line of mean wind direction starting at the estimated maximum distance $X_{max}$ from measurement point P, and iteratively (e.g. using a bisection or other method) moving closer to the measurement point P along the mean wind direction line until the angle $\theta$ subtended by the path segment 79 is sufficient to meet the probability threshold, as determined from the cumulative probability of wind directions over the subtended angle $\theta$, FIG. 11. Referring again to FIG. 4, the survey area indicator 80 may be displayed on the map 70 as a colored "swath" adjoining the path 74 and extending in a substantially upwind direction from the path.

Figure 12:
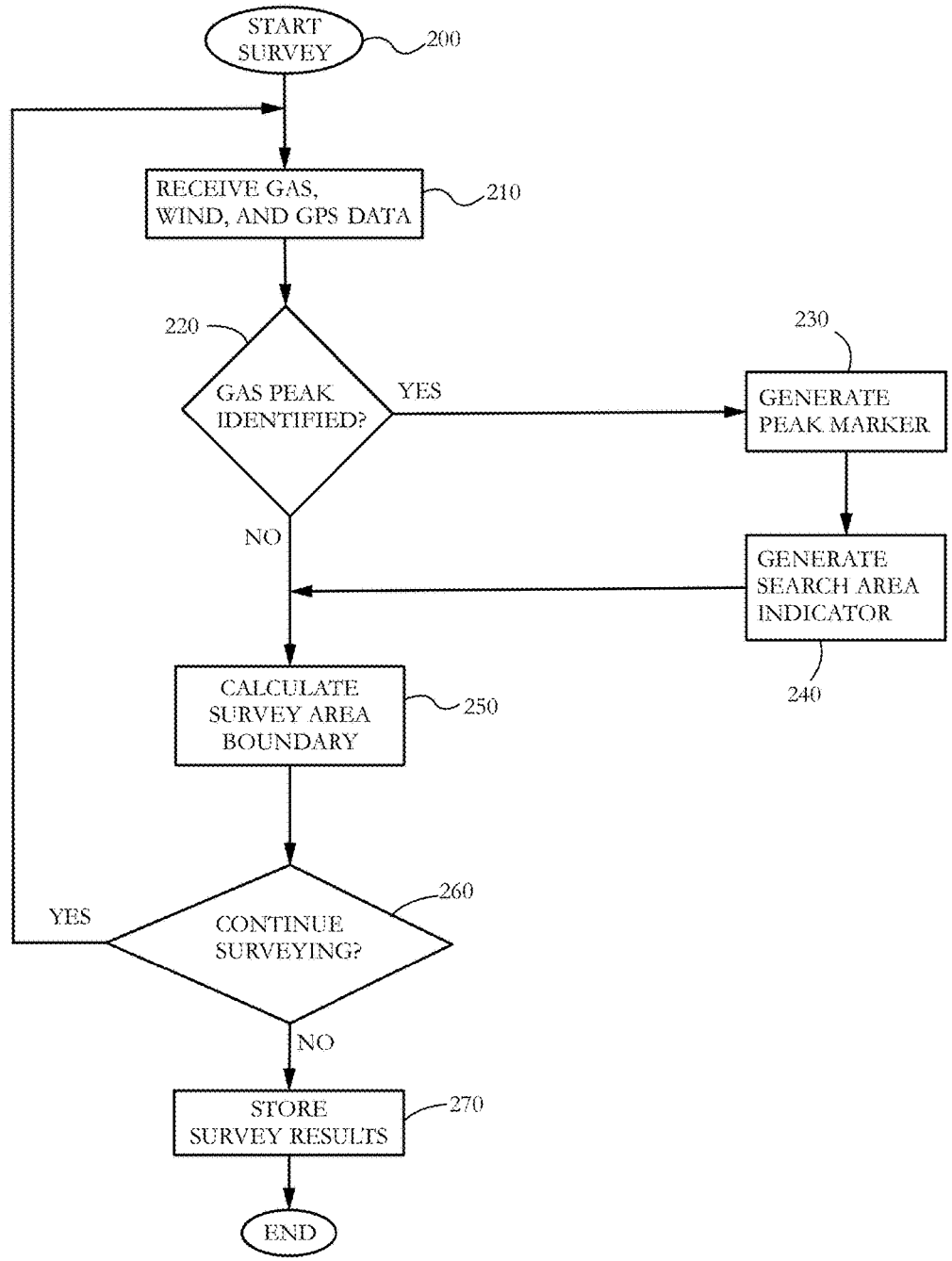
FIG. 12 is a flow chart showing steps for performing a gas leak survey according to some embodiments of the present invention.

FIG. 12 is a flow chart showing a sequence of steps to perform a gas leak survey according to some embodiments of the present invention. In step 200, the survey program is started, for example by an operator in the vehicle using a graphical user interface (GUI). The operator begins to drive the vehicle on a survey route while the GUI displays a street map (FIG. 4). Gas concentration measurements are preferably performed rapidly along the survey route (e.g., at a rate of 0.2 Hz or greater, more preferably 1 Hz or greater). This enables the practice of driving the vehicle at normal surface street speeds (e.g., 35 miles per hour) while accumulating useful data. The gas concentration is measured initially as a function of time, and is combined with the output of the GPS receiver in order to obtain the gas concentration as a function of distance or location. Interpolation can be used to sample the data on a regularly spaced collection of measurement points. The concentration of methane typically varies smoothly with position, for the most part being equal to the worldwide background level of 1.8 parts per million together with enhancements from large and relatively distant sources such as landfills and marshes.

In step 210, at least one processor (e.g. of a client device, server device, or a combination) receives data representative of measured gas concentrations, wind direction measurements, wind speed measurements, and GPS data. In decision block 220, it is determined if a peak in gas concentration is identified. A peak may be identified from a gas concentration measurement above a certain threshold (or within a certain range), or exceeding background levels by a certain amount, which may be predetermined or user-selected. In some embodiments, the gas concentration and GPS data are analyzed using a peak-location method, and then each identified peak is subsequently fit (using linear or nonlinear optimization) for center and width. The functional form used for this fitting step may be a Gaussian pulse, since a Gaussian is commonly the expected functional form taken by gas plumes propagating through the atmosphere.

If a peak in gas concentration is not identified, then the program proceeds to step 250. If a peak in gas concentration is identified, then a peak marker is generated in step 230. The peak marker may be displayed on the map as a user-selectable layer, as previously discussed with reference to FIG. 4. In step 240, a search area indicator is generated to indicate the likely location of a gas leak source corresponding to the identified peak in gas concentration. The search area indicator may be displayed on the map as a user-selectable layer, as shown in FIG. 4. In step 250, the survey area boundary is calculated, and a survey area indicator may be displayed on the map as a user-selectable layer (hatched region in FIG. 4). In decision step 260, it is determined if the operator wishes to continue surveying (e.g., by determining if the "Stop Survey" button has been selected). If yes, the survey program returns to step 210. If not, the survey results are stored in memory in step 270 (e.g., in the survey results 64 of FIG. 3), and the survey program ends.

Figure 13:
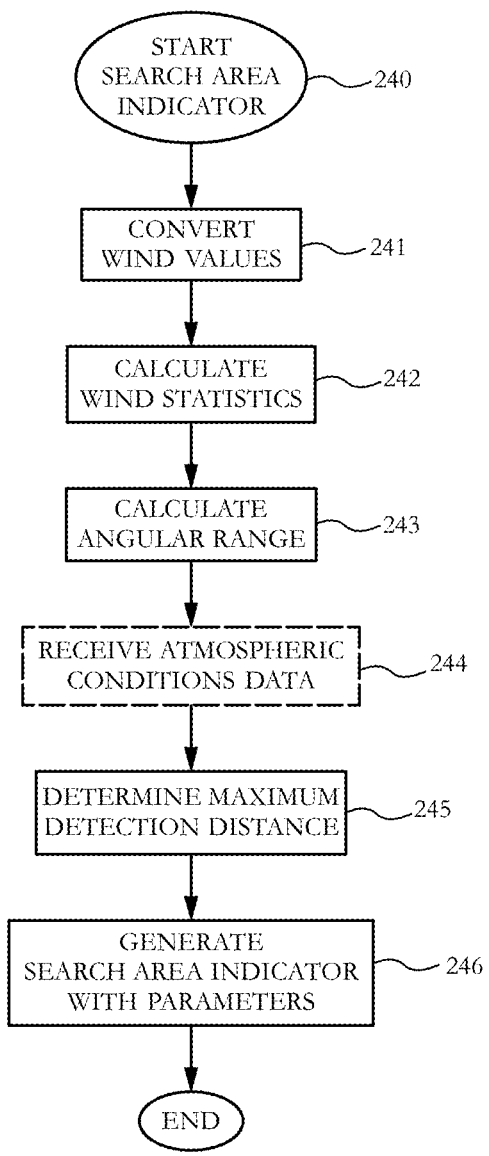
FIG. 13 is a flow chart showing steps for generating a search area indictor according to some embodiments of the present invention.

FIG. 13 is a flow chart showing a sequence of steps performed to generate a search area indicator according to some embodiments of the present invention. When a local enhancement in the gas concentration is detected, the likely direction and estimated distance to the potential gas leak source is preferably calculated from data representative of wind direction and wind speed measured during a time interval just prior to or during which the gas concentration was measured. The time interval is preferably fewer than 2 minutes, and more preferably in the range of 5 to 20 seconds. Calculating statistics from wind measurements may require some conversion if the measurements are made using sensors on a moving vehicle. A sonic anemometer is preferably used to measure wind along two perpendicular axes. Once the anemometer has been mounted to the vehicle, these axes are preferably fixed with respect to the vehicle. In step 241, wind speed and wind direction values that were measured relative to the vehicle are converted to wind speed and wind direction values relative to the ground by subtracting the velocity vector of the vehicle, as obtained from the GPS data. When the vehicle is stationary, GPS velocity may be ineffective for determining the orientation of the vehicle and wind direction, so it is preferable to use a compass (calibrated for true north vs. magnetic north) in addition to the anemometer.

In step 242, wind statistics are calculated from the converted wind values to provide the parameters for the search area indicator. The statistics include a representative wind direction that is preferably a mean, median, or mode of the wind direction measurements. The statistics also include a wind direction variability, such as a standard deviation or variance of the wind direction measurements. In step 243, an angular range of search directions, extending from the location of the gas concentration measurement point where the local enhancement was detected, is calculated according to the variability of the wind direction measurements. In optional step 244, atmospheric conditions data are received. Step 245 is determining a maximum detection distance value representative of the estimated maximum distance from the suspected gas leak source at which a leak can be detected. In some embodiments, the maximum detection distance value is determined according to Equation (3) or Equation (4), and the data representative of wind speed and/or atmospheric stability conditions. Alternatively, the maximum detection distance value may be a predetermined number, a user-defined value, empirically determined from experiments, or a value obtained from a look-up table. In step 246, the search area indicator is generated with the determined parameters, previously discussed with reference to FIG. 8.

Figure 14:
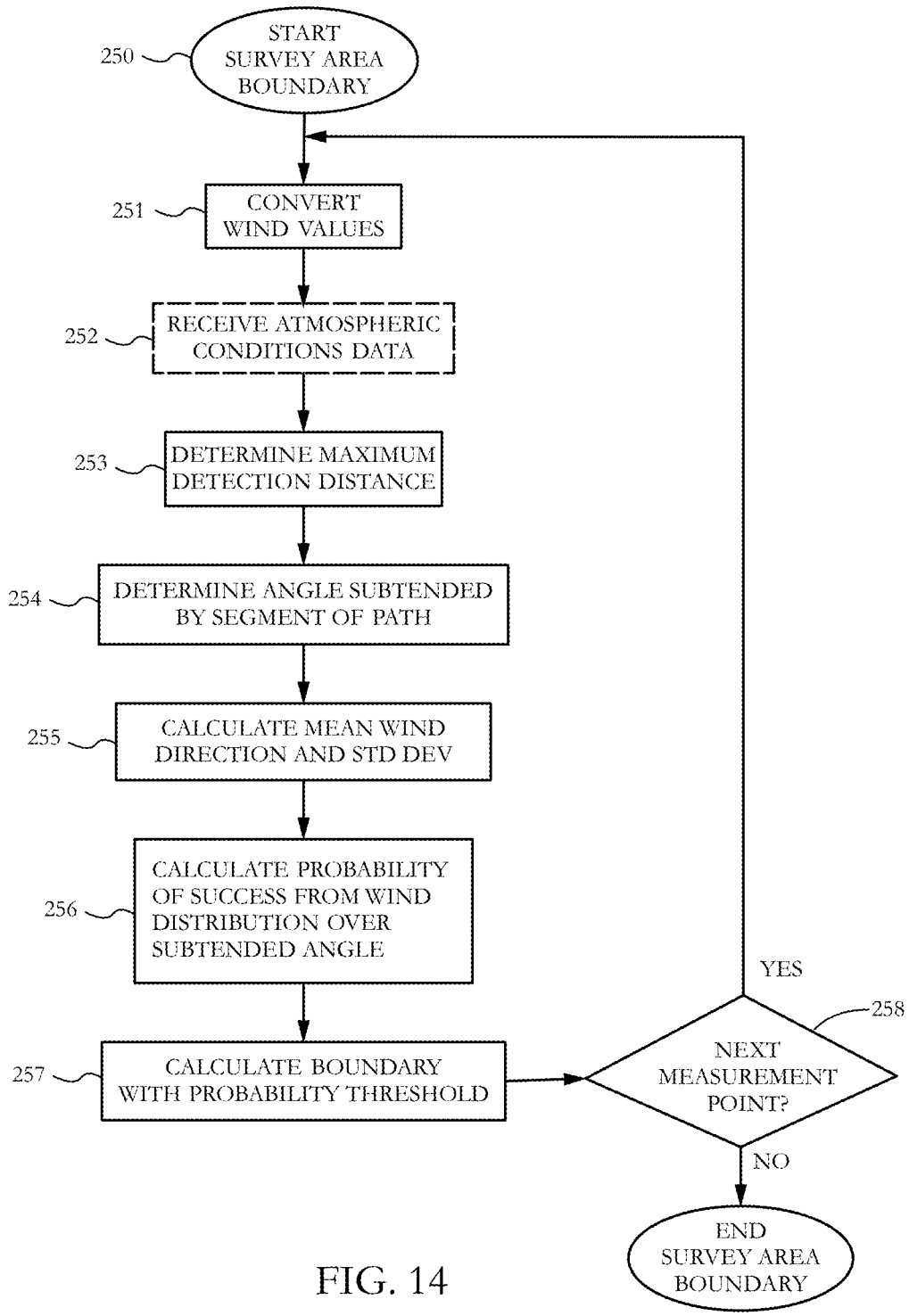
FIG. 14 is a flow chart showing steps for calculating a boundary of a survey area according to some embodiments of the present invention.

FIG. 14 is a flow chart showing a sequence of step performed to calculate a boundary of a survey area according to some embodiments of the present invention. In step 251, wind speed and wind direction values that were measured relative to the vehicle are converted to wind speed and wind direction values relative to the ground by subtracting the velocity vector of the vehicle, as previously described in step 241 above. In optional step 252, atmospheric conditions data are received. Step 253 is determining a maximum detection distance value representative of the estimated maximum distance from a suspected gas leak source at which a leak can be detected. In some embodiments, the maximum detection distance value is determined according to Equation (3) or Equation (4), and the data representative of wind speed and/or atmospheric stability conditions. Alternatively, the maximum detection distance value may be a predetermined number, a user-defined value, empirically determined from experiments, or a value obtained from a look-up table. In step 254, it is determined what angle θ is subtended by a segment of the path of the vehicle relative to the candidate point Q for the potential gas leak source. The path segment is positioned within a distance of the candidate point Q that is less than or equal to the estimated maximum distance.

In step 255, a representative wind direction (e.g., a mean, median, or mode of the wind direction measurements) and a wind direction variability (e.g., variance or standard deviation) are calculated from the wind direction measurements. In step 256, the probability of detection is estimated according to a cumulative probability of wind directions with respect to the subtended angle θ. In step 257, the survey area boundary is calculated with a probability threshold. For example, if the angle θ subtended by the path segment relative to the candidate point encompasses a percentage of possible wind vectors that is greater than equal to a threshold percentage (e.g., 70%), and if the distance from the candidate point Q to the measurement point P is less than the estimated maximum distance $X_{max}$, then the candidate point Q is deemed to be within the survey area. In decision step 258, it is determined if the survey area boundary function is to continue with the next measurement point. If yes, steps 251-257 are repeated as different measurement points along the path are chosen and different candidate points are evaluated for the probability of successful detection of a potential gas leak source. If not, then the boundary function ends.

Figure 15:
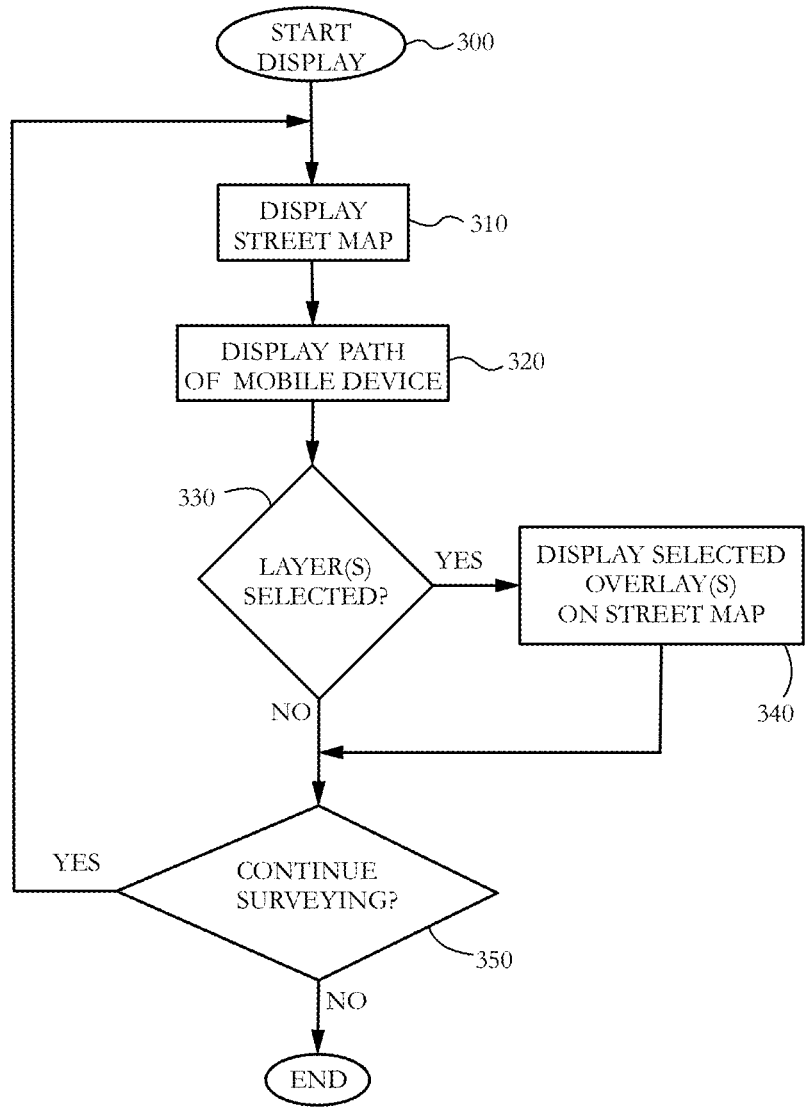
FIG. 15 is a flow chart showing steps for displaying layers overlaid or superimposed on a street map according to some embodiments of the present invention.

FIG. 15 is a flow chart showing steps for displaying layers overlaid or superimposed on a street map according to some embodiments of the present invention. In step 310, a street map is displayed, preferably on a GUI visible to the operator in the vehicle. In step 320, the path of the vehicle with the mobile gas measurement device is displayed on the map. Various elements displayed on the map are regarded as layers which may be turned on or off. In this example, the map controls window (FIG. 7) includes six user-selectable buttons named "Hide Peak Markers", "Hide Search Area Indicators", "Minimum Amplitude", "Hide Isotopic Analysis", "Hide Field of View", and "Hide Plat Outline". In decision step 330, it is determined if one or more of these layers is selected. If yes, the selected layer is displayed overlaid or superimposed on the street map in step 340. If not, it is determined if the survey is to continue. If yes, display steps 310-350 are repeated. If not, the display options may end.

Assembling Peak Collections and Selecting Representative Peaks Characterizing Given Sources In some embodiments, gas emissions and/or atmospheric condition data collected and analyzed as described above may be used to selectively display only some (e.g. one or more) detected peaks believed to originate from a single localized natural gas emission source. A localized emission source may be caused by a leak in a natural gas transmission/distribution pipeline or other transmission/distribution infrastructure (e.g. natural gas meters and associated pipes), or other sources. In many instances, a single leak in a pipeline or other infrastructure emerges from the ground or above-ground surface at a single surface location, although some leaks in underground pipelines may emerge from the ground at multiple surface locations along an area spanning meters to tens of meters or larger. Also, closely-spaced leaks (e.g. leaks separated by a distance on the order of meters) may lead to one or more closely-spaced surface emission points that are not readily distinguishable in a mobile survey, and may be effectively treated as a single leak by exemplary peak collection systems/methods as described below.

Depending on the survey path and the wind direction(s) during the survey, a single emission source may result in the detection of multiple peaks. In particular, in the context of mobile gas leak detection in urban and suburban landscapes, the wind is often channeled by groups of structures such that the path of the survey vehicle aligns (or anti-aligns) with the wind direction (see FIG. 19 for an illustration of an exact anti-alignment). Exemplary systems and methods as described below allow reducing the number of redundant leak indications arising by passing in and out of a plume from one or more leaks. Being able to associate peaks with sources, i.e. being able to tell whether two peaks originate at a single source or different sources, allows simplifying the process of localizing, characterizing and repairing leaks.

Figure 19:
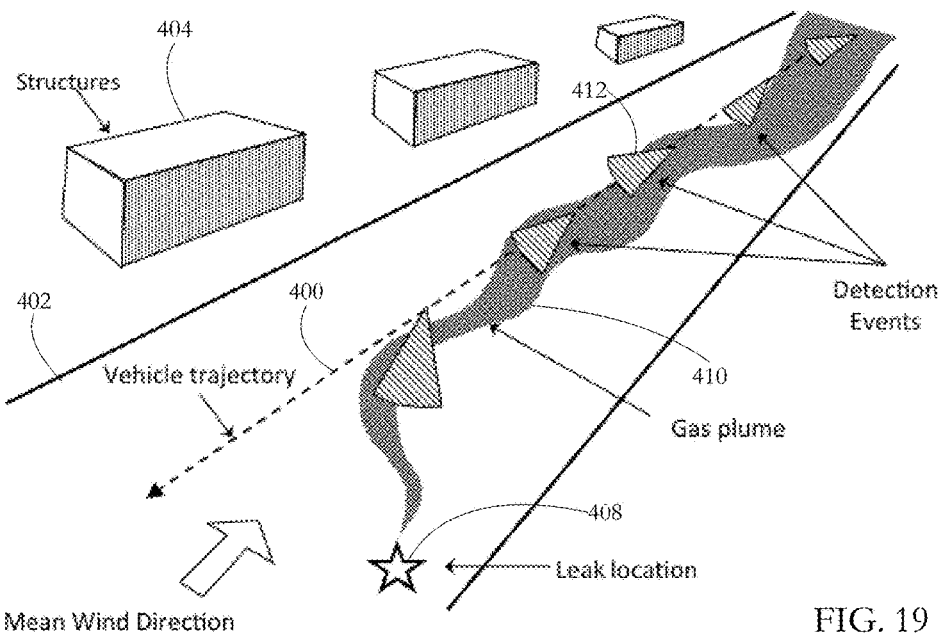
FIG. 19 shows an exemplary survey geometry in which a single source may lead to the detection of multiple peaks along a survey path, according to some embodiments of the present invention.

FIG. 19 shows an exemplary survey geometry in which a single source may lead to the detection of multiple peaks along a survey path, according to some embodiments of the present invention. Consider an exemplary vehicle measurement path (trajectory) 400 along a road 402 bounded on both sides by buildings 404. A localized natural gas emission source (e.g. leak) 408 emits a gas plume 410 which may generally meander along the general direction of road 402. A survey vehicle traveling along vehicle path 400 may detect a plurality of sequential detection events, represented in FIG. 19 by corresponding search area indicators 412, all characterizing source 408.

Systems and methods described below facilitate the characterization of such multiple detection events as associated with (i.e. originating from) a single emission source rather than multiple distinct leaks originating from different locations. In the discussion below, an event is the detection of a peak in an observed methane concentration versus distance traveled along the survey path. As described above, each event comprises the georeferenced (e.g. GPS) position where the plume detection occurred. Other event information may additionally include, without limitation, one or more of the following: the distance traversed by the vehicle at the time when the detection occurred, as defined with respect to a specified origin (e.g. the start of the survey); the amplitude of the plume, defined as the gas concentration minus the ambient background concentration; a measure of the spatial extent (width) of the plume as transected by the path of the vehicle (for example, as determined using horizontal spatial scale analysis); the mean (or other representative value) wind speed, direction, and/or direction variability computed in a window of time leading up to the plume detection event; and the compass bearing of the vehicle at the time when the gas plume was detected.

Figure 20:
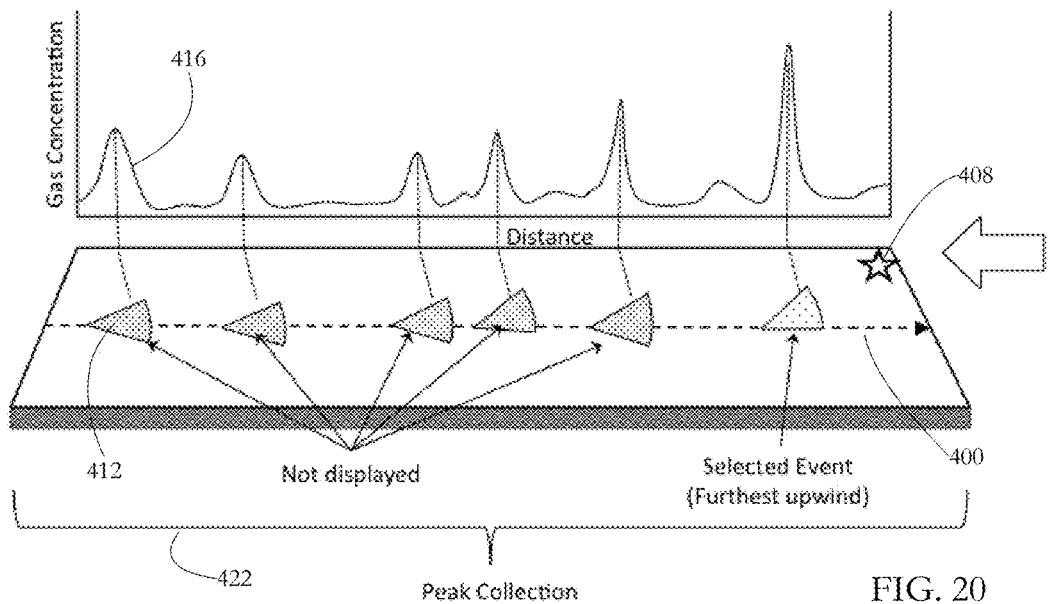
FIG. 20 shows an exemplary correspondence between detected natural gas concentration peaks and associated search area indicators along a measurement path, according to some embodiments of the present invention.

FIG. 20 shows an exemplary correspondence between detected natural gas concentration peaks and associated search area indicators along a measurement path, according to some embodiments of the present invention. Each of a plurality of detected natural gas concentration peaks 416 detected along vehicle trajectory 400 corresponds to a search area indicator 412. The plurality of peaks 416 assigned to a single, common emission source 408 are assigned to a peak collection 422 as described below. In some embodiments, assigning peaks to a collection proceeds iteratively, by considering a new (candidate) peak in relation to one or more peaks in an existing collection assigned to a common emission source. Two peaks may be associated in a collection according to an inter-peak distance, a representative wind direction and/or wind variability at one or both of the peak locations, and/or other factors. Such factors may include, without limitation, the spatial extent (width) of the two peaks; the angle between the compass bearing of the vehicle and that of the representative (e.g. mean) wind direction, with the representative wind direction being computed over a window of time leading up to detection of the event furthest downwind; the variability of the measured wind direction computed over a window of time leading up to the detection of the event; the compass bearing between the downwind event and the upwind event; the instantaneous wind speed as measured when one or both events were detected; one or more indicators of atmospheric stability, such as measurements of incoming solar radiation, energy radiated by the ground, amount of cloud cover, wind speed, pressure, or temperature; information about the likely origin of the leak, such as a map of the distribution infrastructure; and information about the context of the measurement such as the type of terrain, density of buildings, or surface material (e.g. asphalt, concrete, dirt).

In particular, in some embodiments multiple peaks are assigned to a common emission source according to a proximity (or overlap) condition dependent on an inter-peak distance, and a wind direction and variability condition dependent on wind variability and a directional relationship between a representative wind direction and a direction of motion of the measurement vehicle. Two peaks that satisfy the proximity and wind conditions are grouped together, while two peaks that do not satisfy both conditions are deemed to potentially represent different emission sources and are not grouped together. In addition, one or more pre-filters may be applied to classify individual plume detection events as likely originating from a nearby, localized gas plume rather than from fluctuations of the ambient concentration level. For example, an auto-threshold filter may be applied to filter out peaks whose amplitude does not exceed a local background variability. The local background variability may be measured by a standard deviation of the concentration, filtered or unfiltered, across a given number of recorded samples immediately preceding a current sample. For example, a filter that returns the minimum value of the concentration in a moving window of a chosen fixed distance may be applied to attain a more accurate measure of the background concentration in the presence of narrow concentration peaks arising from nearby sources. A standard deviation of the filter output may be taken to represent a measure of the background variability. One may then require that the amplitude of a peak exceed a threshold that is a fixed multiple of the background variability, or a multiple of the background variability that also depends on other properties of the peak in addition to amplitude, such as its width.

Figure 21:
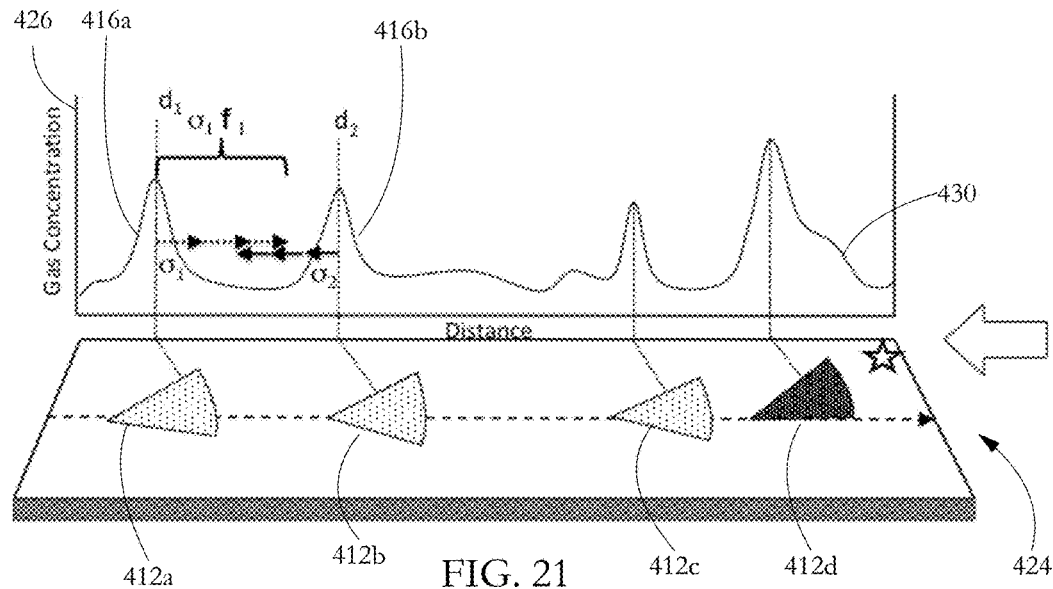
FIG. 21 illustrates a grouping of peaks according to a proximity condition according to some embodiments of the present invention.

FIG. 21 illustrates a grouping of peaks according to a proximity condition according to some embodiments of the present invention. A top panel 424 shows a sequence of search area indicators 412a-d superimposed on a street view of the corresponding locations, while a bottom panel 426 shows a concentration function 430 illustrating the variation of measured methane concentration with position over the vehicle measurement path. According to some embodiments, a proximity condition for two adjacent (immediately-neighboring) peaks 416a-b is determined according to a distance relationship between directionally-scaled measures of the peak widths, and in particular to whether the directionally-scaled peak widths overlap. For example, the adjacent peaks 416a-b situated at locations (coordinates) $d_1$ and $d_2$ are deemed to meet the proximity condition (or overlap) if, in the case of a direction of motion that is generally anti-aligned with the wind direction (as illustrated in FIG. 21), $$d_1 + f_1 \sigma_1 > d_2 - f_2 \sigma_2 \quad [5]$$

wherein $\sigma_1$ and $\sigma_1$ are measures of the widths of the two peaks, respectively, and $f_1$ and $f_2$ are direction-dependent scaling (overlap) factors. Such an overlap is illustrated schematically for peaks 416a-b in FIG. 21. If the direction of motion and representative wind direction are generally aligned, rather than anti-aligned, the sign of the inequality in eq. [5] changes to <(less than). A peak's scaling factor determines its effective spatial influence: a large scaling factor will lead to a peak being deemed overlapping even if physically further away from a neighboring peak, while a smaller scaling factor requires closer physical proximity between two adjacent peaks before the peaks are deemed to belong to the same collection/source.

In some embodiments, a wind condition is met if the downwind event (peak) points toward the location of the upwind event (peak) to within a measure of the pointing uncertainty of the downwind event. Such a wind condition may be expressed as $$u_1 \cdot b_{12} > \cos \theta_1 \text{ or } \theta_1 > \pi \quad [6]$$

wherein $u_1$ is a unit vector representing the most likely direction from the first (downwind) event to the location of the emission source (e.g. a representative wind direction during a window of time leading up to and/or around the peak detection), $b_{12}$ is a unit vector pointing from the location of the downwind event to the location of the upwind event, and $\theta_1$ is an uncertainty in the direction from the downwind location to the emission source location. The first term of eq. [6] applies when $\theta_1 < \pi$, when the wind is anti-aligned with the direction of motion of the measurement device.

The uncertainty in direction may include terms accounting for an uncertainty in reconstructed representative (e.g. mean) ground wind speed and direction due to measurement errors, as well as uncertainty due to variability of the wind direction. In some embodiments, in order to calculate the true ground wind speed and direction, the actual wind speed and direction as measured on-board the moving vehicle are corrected for the vehicle's motion and for how the vehicle affects the flow of air above it where the wind measurement is made. The wind measurement from the anemometer carries an uncertainty that is proportional to the measured wind speed. The effects of the vehicle on the airflow above the vehicle can be accounted for using a correction term that is measured, and which also has an associated uncertainty. The uncertainty in the ground wind speed and direction due to these two measurement uncertainties can be modeled using a simulation. The simulation can be used to create a model that parameterizes the degree of uncertainty as a function of the speed of the vehicle and magnitude of the ground wind speed. In such a model, this uncertainty may vary directly with the speed of the vehicle, and inversely with the wind speed.

In some embodiments, the scaling (overlap) factor f assigned to each peak may be chosen to be fixed or variable. In an exemplary embodiment particularly suitable for situations in which wind is channeled by structures (see the geometry of FIG. 19), for each pair of adjacent peaks under analysis, the upwind peak scaling factor is taken to be fixed, while the downwind peak scaling factor is chosen to be variable and determined as described below.

For the upwind peak, the scaling factor may be chosen to simply describe the physical extent of the peak. An exemplary fixed scaling factor may have a value between 2 and 5, for example about 3. For a Gaussian peak, a scaling factor of 3 captures more than 99% of the extent of the peak. For the downwind peak, the scaling factor may be chosen to give the peak a longer reach when the peak points more closely to the upwind peak location. Such a scaling factor may take into account both direction and variability in direction: if the wind direction is more variable, there is a greater chance that two adjacent events are unrelated, i.e. do not originate from the same source.

Figure 22:
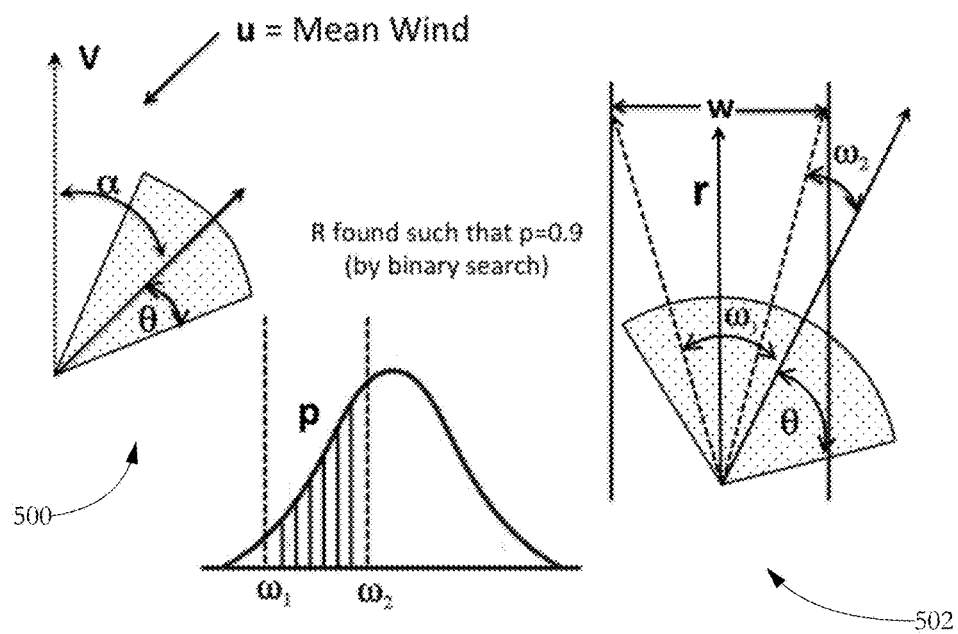
FIG. 22 illustrates an exemplary model for determining a variable downwind peak scaling factor according to both wind direction and wind variability, according to some embodiments of the present invention.

FIG. 22 illustrates an exemplary model for determining a variable downwind peak scaling factor according to both wind direction and wind variability, according to some embodiments of the present invention. Consider a measurement vehicle traveling along a direction defined by a vector v, with the wind characterized by a representative wind direction u and a wind variability angle $\theta$, and with $\alpha$ denoting the angle between the vectors v and u, as shown generally at 500 in FIG. 22. The vector v, characterizing the vehicle direction of motion with respect to ground, and the vector u, characterizing the representative wind direction with respect to ground, may be expressed in terms of scalar components as ($v_E$, $v_N$) and ($u_E$, $u_N$), respectively. The angle $\alpha$ between the vehicle's direction of motion and the inter-point direction may then expressed as $$\alpha = \tan^{-1}\left(\frac{v_E}{v_N}\right) - \tan^{-1}\left(\frac{u_E}{u_N}\right) \quad [7]$$

Consider now a line segment of length w, perpendicular to the vehicle direction of motion v, and situated a distance r ahead of the vehicle's position, as shown generally at 502 in FIG. 22. The forward reach of the downwind peak may be determined according to the probability that the downwind event points to a point along the line segment at a distance r ahead. A downwind event pointing to a point ahead is equivalent to wind from the point ahead passing through the location of the downwind event. That probability may be expressed as a function of two angles, $\omega_1$ and $\omega_2$, shown in FIG. 22:

$$\omega_1 = -\tan^{-1}\left(\frac{w}{2r}\right) - \alpha \quad [8a]$$

$$\omega_2 = \tan^{-1}\left(\frac{w}{2r}\right) - \alpha \quad [8b]$$

If the error in event pointing certainty is Gaussian, the probability that an event points to a location along the line segment a distance r ahead can be estimated as:

$$p = \frac{1}{2}\left(\operatorname{erf}\left(\frac{\omega_2}{\sqrt{2}\,\theta}\right) - \operatorname{erf}\left(\frac{\omega_1}{\sqrt{2}\,\theta}\right)\right) \quad [9]$$

where erf(x) is the Gaussian error function.

Using equation [9], a particular value of r that leads to a desired value of p (e.g. p=0.9, or a probability of 90%) may be found by a technique such as a binary (half-interval) search. In such a method, a search key is compared to the middle of a current evaluation range, and the upper or lower halves of the range are selected as a new evaluation range according to the comparison. For example, in an exemplary binary search method starting with a value of r of 100 m, if the value is too large to yield p=0.9 according to eq. [9], r is halved to 50 and a new evaluation is performed (r is doubled otherwise). If a value of r=50 is too small to yield p=0.9 according to eq. [9], then r is set to 75 and reevaluated, while if r=50 is too large, r is set to 25 and reevaluated. The search process then continues, with the relevant search intervals halved at each step until a suitable value of r is found. The value of r may be deemed suitable if it approaches the desired value to within a predefined tolerance that is small compared to the range of values searched. In some embodiments, a search tolerance of 0.1-1.0 m may be acceptable.

A suitable scaling factor f may be set to be proportional to the value of r that yields a desired, predetermined probability, i.e. f=ar, where a is a fixed constant. If no value of r that yields the predetermined probability is found, r may be set to a predetermined minimum value. In an exemplary embodiments, a minimum value of r may be chosen to achieve a minimum value of f between 2 and 4, for example about 3, for the downwind peak.

FIG. 23-A-B show scaling (overlap) factors for downwind peaks as a function of θ and α, respectively, computed according to eq. [9] according to some embodiments of the present invention. FIG. 23-A shows computed scaling factor values as a function of θ (one-sigma opening angle) for several values of α, while FIG. 23-B shows computed scaling factor values as a function of a for several values of θ. As illustrated, smaller values of θ and α generally correspond to larger scaling (overlap) factor values.

In some embodiments, one or more fixed, amplitude- and/or distance-dependent constraints are imposed on the assignment of peaks to a given collection. For example, in some embodiments two peaks separated by a distance less than a predetermined minimum distance are automatically considered to be overlapping, regardless of wind direction. The minimum distance may be between 1 and 20 m, more particularly between 5 and 15 m, for example about 10 m. At the same time, a new peak must be within a predetermined maximum distance of all existing peaks in a collection in order to be eligible to be added to the collection. The predetermined maximum distance may be between 50 and 200 m, for example about 100 m. This maximum distance may be chosen to be of similar magnitude as the typical maximum distance from which a source may be detected, and acts as a safety measure so that the process doesn't associate events that are greatly separated in distance with a single source, even in the presence of bridging peaks. For example, if a new peak is within 10 m of an existing peak but not within 100 m of all other peaks in the collection, a new collection may be started.

In some embodiments, if f>3, an upwind peak must fall within a one-sigma variability indicator of the downwind peak, or within a minimum configurable opening angle, for example about 30°, of the downwind peak, to be considered overlapping with the downwind peak. Requiring the upwind peak fall within the pointing uncertainty of the downwind peak ensures correct behavior for large values of f if the path of the vehicle is curved, as events are not collected if the path is strongly curved. If the scaling distance r is determined, as described above, by looking directly ahead of the vehicle, the upwind event should lie along an approximately straight-line path ahead of the downwind event in a pair. For lower values of f (3 and below), it may be deemed acceptable to associate nearby peaks even if the path of the vehicle is curved.

After a peak collection has been assembled, one or more filters are applied to filter out at least some of the peaks of the collection, and thus select a representative subset of peaks to be displayed to a user. In some embodiments, a selection method may include, but is not limited to, of one or more of the following operations: selecting the event occurring furthest upwind, selecting the event with the largest amplitude, and selecting an event if its amplitude exceeds a predetermined minimum threshold. Always selecting all events with relatively high amplitudes and the event with the largest amplitude in a collection, regardless of upwind/downwind relative positioning relative to other peaks, accounts for the possibility that there may be more than one source giving rise to the indications in the collection. Since nearby sources tend to give rise to larger amplitude indications than those farther away from the survey path, a large-amplitude peak originating from one source may be grouped together in a collection with peaks originating from another source further upwind. In addition, one or more pre-filters may be applied to classify individual plume detection events as likely originating from a nearby, localized gas plume rather than from fluctuations of the ambient concentration level. Experience has shown that below a certain amplitude threshold, which may vary as a function of the variability of the ambient concentration, events are unlikely to contain information that is useful for pinpointing a source, but such events may still be useful for linking one peak to another within a collection via successive applications of the collection-building steps described above. The primary output of such a selection method is information (e.g. a subset of plume detection events, and other associated information) most relevant for efficiently finding leaks associated with assembled groups of leak detection events.

An amplitude threshold filter may be used to filter out peaks below a determined threshold to yield a first subset of qualifying peaks. For example, peaks greater than a minimum amplitude (e.g. 0.02-1 ppm, more particularly 0.02-0.1 ppm, for example about 0.03 ppm relative to a local background level) but that are too small to pass a threshold filter can be members of the collection but are not eligible for display. In some embodiments, the most upwind qualifying peak in a collection is always selected for display, even if it is not the largest peak in the collection. Additionally, the peak with the largest amplitude in the collection is always selected for display, even if it not the most upwind peak in the collection. In practice, the most upwind peak is often the peak with the highest amplitude in a collection, but that need not always be the case. Furthermore, in some embodiments any peak with an amplitude exceeding a predetermined threshold is always displayed, even if it is not the largest or most upwind; such an exemplary threshold may have a value of 1-20 ppm, for example 5 ppm above the local background level. The different types of peaks described above (highest-amplitude, most-upwind, and above-threshold) may be displayed with different graphic properties such as color and/or shape, to allow a user ready visual identification of the reason(s) the peak was selected for display.

Figure 24:
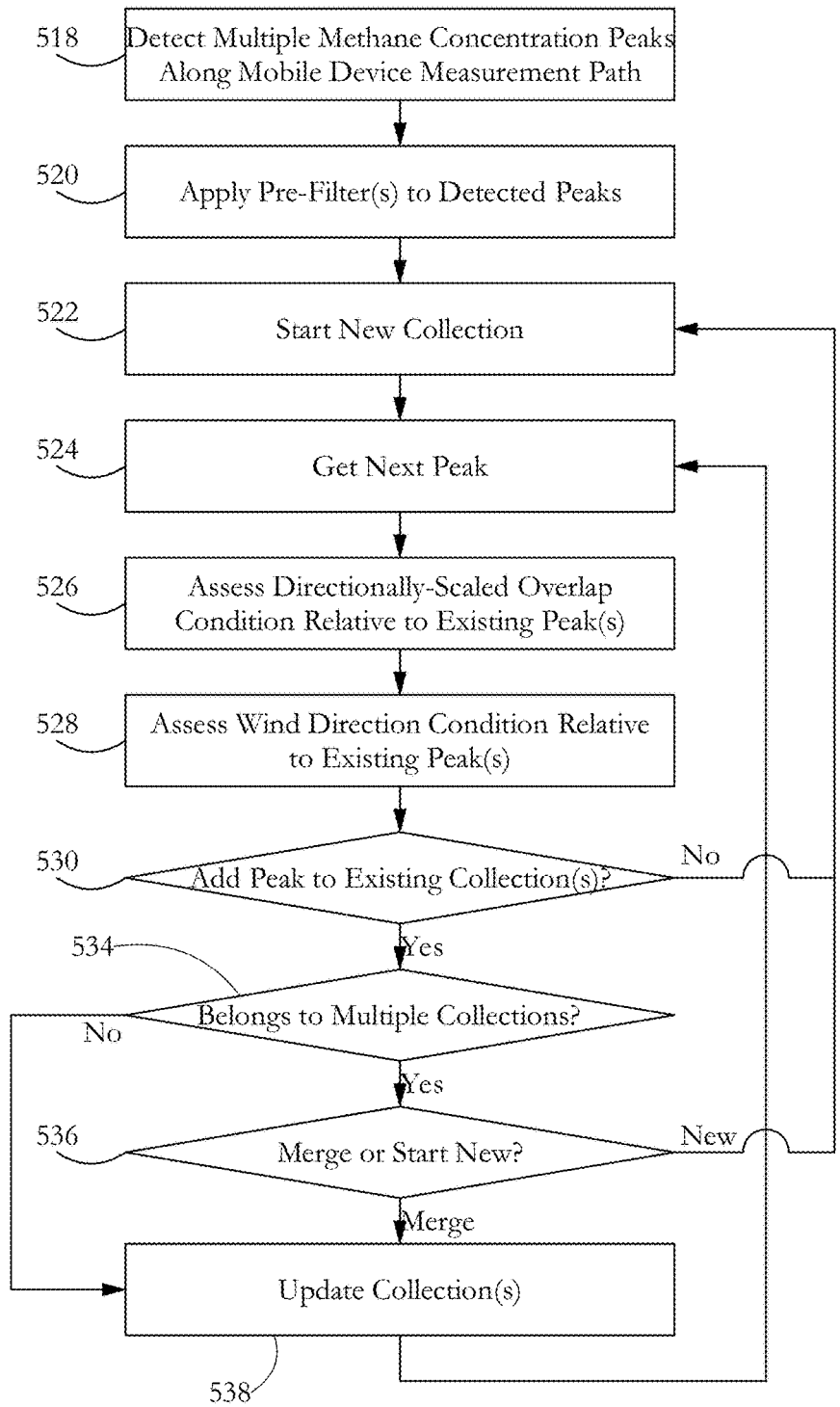
FIG. 24 is a flowchart illustrating a number of steps performed to assemble a peak collection assigned to single natural gas emission source according to some embodiments of the present invention.

FIG. 24 is a flowchart illustrating a number of steps performed to assemble a peak collection assigned to single natural gas emission source according to some embodiments of the present invention. In a step 518, multiple methane concentration peaks are detected along a mobile measurement path as described above. In a step 520, one or more pre-filters are applied to the detected peaks as described above. In a step 522, a new collection is started with the first detected peak in the measurement sequence. In a step 524, the next recorded peak in the sequence is retrieved in order to determine whether the peak should be added to the existing collection(s). In subsequent steps 526, 528, a directionally-scaled overlap condition and a wind direction condition as described above are assessed, respectively, for the current peak in relation to the existing peaks in the current collection and previous collections. All preceding peaks are evaluated to determine whether the new peak falls within the maximum allowable spatial extent (e.g. 100 m) of the collection. At the same time, if the spatial extent condition is met, the new peak is considered to belong to the collection if it meets the overlap and wind direction conditions with respect to at least one existing peak in the collection. In a step 530, it is determined whether the current peak should be added to at least one existing collection, whether the current collection or any other previous collections. If the peak is not added, a new collection is started (step 522) and the process proceeds as described above for the new collection.

The peak is deemed to tentatively belong to an existing collection if both conditions assessed in steps 526, 528 are met, and does not belong otherwise. If the peak is found to tentatively belong to at least one existing collection, the process proceeds to a step 534. In step 534, it is determined whether the peak tentatively belongs to more than one collection. If the peak belongs to a single collection, the collection is updated (step 538), and the process proceeds to assess the next peak (step 524). If the peak belongs to more than one collection, it is determined in a step 536 whether the two collections should be merged. The two collections are merged as long as the resulting collection does not exceed the maximum allowable spatial extent for the merged collection size. If the collections are merged, the peak is added to the merged collection and the collection data is updated (step 538). If the resulting merged collection would exceed the maximum spatial extent of a collection, the collections are not merged, and a new collection is started.

(step 522) The sequence described above is useful particularly because it is possible that a narrow peak does not overlap a collection, so a new collection is started, but the next peak may have a larger width, and so does overlap the previous collection. In that situation, the two collections may be merged.

Figure 25:
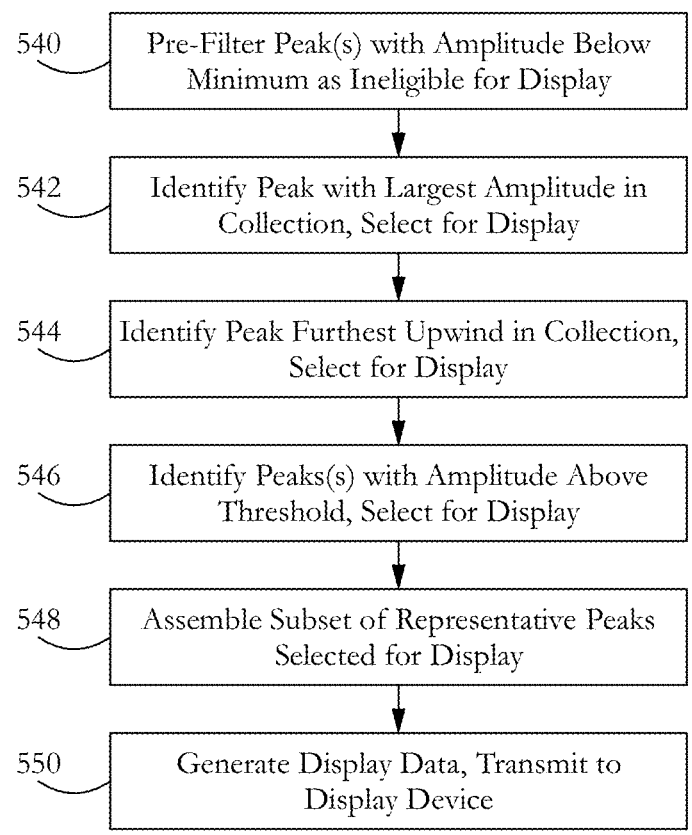
FIG. 25 is a flowchart illustrating a number of steps performed to filter and selectively display a subset of representative peaks from an assembled peak collection according to some embodiments of the present invention.

FIG. 25 is a flowchart illustrating a number of steps performed to filter and selectively display a subset of representative peaks from an assembled peak collection according to some embodiments of the present invention. In a step 540, peaks with an amplitude below a minimum threshold are pre-filtered as ineligible for display as described above. In a step 542, the peak with the largest amplitude in the collection is identified and selected for display. In a step 544, the peak furthest upwind in the collection is identified and selected for display. It is commonly the case that either the first or last peak in the collection is the furthest upwind, but situations can occasionally arise where this is not the case, for example when the path of the vehicle is curved and the wind direction is roughly perpendicular to the vehicle path. In some embodiments, to decide if peak 1 is upwind of peak 2, a line may be drawn perpendicular to the representative wind direction associated with peak 2, through the location of peak 2. If peak 1 lies on the side of the line in the direction the search area indicator points, then peak 1 is upwind of peak 2. In some embodiments, in the unlikely event that the wind direction shifts quickly and the approach above leads to a conclusion that both peaks are upwind of each other, a new collection may be started if such a peak is found. To implement a check ensuring that a peak collection may not have two peaks that are both upwind of each other, the collection assembly steps shown in FIG. 24 may be modified to add a determination of upwind/downwind relationship(s) whenever a decision is made to start a new collection or add a peak to an existing collection.

The peak furthest upwind may also be, but need not be, the peak with the largest amplitude. In a step 546, any peaks with an amplitude above a predetermined threshold are identified and selected for display. Some of the peaks identified in step 546 may also be the largest-amplitude and/or the further upwind peak(s) identified previously. In a set 548, the complete subset of representative events/peaks for the present collection is assembled. In a step 550, display data for the selected subset of events is generated and transmitted to a display device for display to a user. The display data may include geo-referenced graphical representations of the events as described above. In some embodiments, a user interface may include a field configured to accept user input that switches between display modes, with a first display mode displaying all recorded peaks, and a second display mode displaying only a representative subset of peaks as described above.

CONCLUSION

Systems and methods as described above facilitate the location of natural gas leaks and other localized emission sources, particularly in urban environments or other environments in which a measurement sequence taken over a measurement path can lead to the detection of multiple concentration peaks which may originate from a single source or multiple sources. In the context of mobile gas leak surveying, gas plumes from nearby (<100 m) sources are typically very narrow in width compared to the typical length scales associated with turbulent diffusion. The plume can remain narrow in width as it propagates downwind in a "meandering" fashion, its motion lateral to the mean wind direction being driven by larger turbulent eddies. In urban, suburban, or other terrain where structures can channel the wind, a mobile survey vehicle may fully traverse the meandering path of the plume multiple times when approaching or receding from a point source location. Such a measurement frequently leads to multiple leak indications being registered from the same plume at multiple locations along the trajectory of the survey vehicle within a few hundred meters of the point source. When conducting a walking survey to locate sources of gas based on indications generated using mobile survey equipment, investigating multiple indications arising from a single gas source results in longer leak search times. The exemplary systems and methods described above allow recognizing patterns of leak indications that commonly arise from the same point source when traveling into, or in the same direction as, the wind. Exemplary systems and methods described above further allow deciding how to display information most relevant to efficiently finding a leak when searching for the leak by ground survey. In particular, in one approach, a subset of indications which contain the most useful information is selected from a larger set of indications, thus reducing the search area and the amount of time needed for a human operator to pinpoint the leak.

It will be clear to one skilled in the art that the above embodiments may be altered in many ways without departing from the scope of the invention. For example, gas leaks may include, but are not limited to: leaks from gas pipes or transportation systems (e.g., natural gas leaks), leaks from gas processing or handling facilities, and emissions from gas sources into the environment (e.g., pollution, gas emission from landfills, etc.). Gas concentration measurements are preferably performed rapidly (e.g., at a rate of 0.2 Hz or greater, more preferably 1 Hz or greater). This enables the concept of driving a vehicle at normal surface street speeds (e.g., 35 miles per hour) while accumulating useful gas concentration and wind measurement data. However, embodiments of the invention do not depend critically on the gas detection technology employed. Any gas concentration measurement technique capable of providing gas concentration measurements can be employed in some embodiments.

Although the gas concentration measurements are preferably performed while the gas measurement device is moving, at least some gas concentration measurements can be performed while the gas concentration measurement device is stationary. Such stationary gas concentration measurements may be useful for checking background gas concentrations, for example. While real-time measurements are preferred, post analysis of more sparsely sampled data, e.g., via vacuum flask sampling and later analysis via gas chromatography or other methods, may be used in some embodiments. Optionally, measurements can be made on different sides of the road or in different lanes to provide more precise localization of the leak source. Optionally, the present approaches can be used in conjunction with other conventional methods, such as visual inspection and/or measurements with handheld meters to detect emitted constituents, to further refine the results. Optionally, measurements can be made at reduced speed, or with the vehicle parked near the source, to provide additional information on location and/or source attribution.

Optionally, the system can include a source of atmospheric meteorological information, especially wind direction, but also wind speed or atmospheric stability conditions, either on-board the vehicle or at a nearby location. The stability of the atmospheric conditions can be estimated simply from the wind speed, the time of day, and the degree of cloudiness, all of which are parameters that are available either on the vehicle or from public weather databases. Optionally, the computer system can include an on-board video camera and logging system that can be used to reject potential sources on the basis of the local imagery collected along with the gas concentration and wind data. For example, a measured emissions spike could be discounted if a vehicle powered by natural gas passed nearby during the measurements. Optionally, repeated measurements of a single location can be made to provide further confirmation (or rejection) of potential leaks. Accordingly, the scope of the invention should be determined by the following claims and their legal equivalents.

It will be clear to one skilled in the art that the above embodiments may be altered in many ways without departing from the scope of the invention. Accordingly, the scope of the invention should be determined by the following claims and their legal equivalents.

What is claimed is:

1. A computer system comprising at least one processor and associated memory configured to:
   group a plurality of measured natural gas concentration peaks into a collection assigned to a single natural gas leak, the peaks being defined by natural gas concentration data measured by a mobile gas concentration measurement device carried by a vehicle along a survey path, the vehicle carrying a positioning device configured to determine geospatially-referenced locations of gas concentration measurement points along the survey path, the vehicle further carrying a wind direction determination device configured to measure wind direction values along the survey path, wherein grouping the plurality of peaks is performed according to an inter-peak distance determined according to geospatially-referenced locations measured by the positioning device, and further according to a representative wind direction characterizing a measurement of the natural gas concentration data, the representative wind direction being determined according to the wind direction values measured along the survey path; and
   select for display a subset of representative peaks characterizing the natural gas leak, wherein the collection includes at least one peak not selected as a representative peak for display.

2. The computer system of claim 1, wherein each of the peaks of the collection overlaps at least one other peak of the collection.

3. The computer system of claim 1, wherein grouping the plurality of peaks is performed according to a scaling factor for a peak, the scaling factor characterizing a spatial reach of the peak.

4. The computer system of claim 3, wherein the scaling factor is directionally-dependent.

5. The computer system of claim 3, wherein the scaling factor depends on a wind direction characterizing the peak.

6. The computer system of claim 3, wherein the scaling factor depends on a wind variability characterizing the peak.

7. The computer system of claim 3, wherein the scaling factor is determined according to an upwind distance r meeting a probability condition, the probability condition characterizing a probability that the peak points to a location along a transverse line segment of a predetermined width situated a distance r upwind of the peak location.

8. The computer system of claim 1, wherein grouping a new peak into the collection comprises:

determining whether the new peak meets an overlap condition with respect to at least one peak of the collection; and determining whether the new peak meets a wind direction condition with respect to the at least one peak of the collection;

wherein the new peak is assigned to the collection in response to determining that the new peak meets both the overlap condition and the wind direction condition.

9. The computer system of claim 8, wherein determining whether the new peak meets the overlap condition comprises comparing $d_1+f_1\sigma_1$ and $d_2-f_2\sigma_2$, wherein each of the indexes 1 and 2 represent one of the new peak and the at least one peak of the collection, d represents a position of the corresponding peak, f represents a scaling factor characterizing a spatial reach of the corresponding peak, and $\sigma$ represents a width of the corresponding peak.

10. The computer system of claim 8, wherein determining whether the new peak meets the wind direction condition comprises comparing a vector product $u_1 \cdot b_{12}$ to a function of an uncertainty in wind direction, wherein $u_1$ is a representative wind direction vector, and $b_{12}$ is a vector between a location of the new peak and a location of the at least one peak of the collection.

11. The computer system of claim 1, wherein selecting for display the subset of representative peaks comprises identifying a highest-amplitude peak in the collection, and, in response, selecting the highest-amplitude peak for display.

12. The computer system of claim 1, wherein selecting for display the subset of representative peaks comprises identifying a most-upwind peak in the collection, and, in response, selecting the most-upwind peak for display.

13. The computer system of claim 1, wherein selecting for display the subset of representative peaks comprises identifying any peaks having amplitudes exceeding a predetermined amplitude threshold, and, in response, selecting any identified peaks for display.

14. The computer system of claim 13, wherein the predetermined amplitude threshold has a value between 1 ppm and 20 ppm above a local background.

15. The computer system of claim 1, wherein the subset of representative peaks comprises a plurality of representative peaks.

16. The computer system of claim 1, further comprising employing the at least one processor to generate display data for displaying the subset of representative peaks to a user.

17. The computer system of claim 16, wherein the display data comprises, for each peak in the subset, a graphic identifier of a criterion used to select said each peak in the subset for display.

18. The computer system of claim 1, wherein the wind direction values measured along the survey path comprise wind direction values relative to the vehicle, and wherein determining the representative wind direction according to the wind direction values measured along the survey path comprises converting wind direction values relative to the vehicle into wind direction values relative to ground, and determining the representative wind direction according to the wind direction values relative to ground.

19. A non-transitory computer-readable medium encoding instructions which, when executed by a computer system comprising at least one processor, cause the at least one processor to:

group a plurality of measured natural gas concentration peaks into a collection assigned to a single natural gas leak, the peaks being defined by natural gas concentration data measured by a mobile gas concentration measurement device carried by a vehicle along a survey path, the vehicle carrying a positioning device configured to determine geospatially-referenced locations of gas concentration measurement points along the survey path, the vehicle further carrying a wind direction determination device configured to measure wind direction values along the survey path, wherein grouping the plurality of peaks is performed according to an inter-peak distance determined according to geospatially-referenced locations measured by the positioning device, and further according to a representative wind direction characterizing a measurement of the natural gas concentration data, the representative wind direction being determined according to the wind direction values measured along the survey path; and select for display a subset of representative peaks characterizing the natural gas leak, wherein the collection includes at least one peak not selected as a representative peak for display.

20. The non-transitory computer-readable medium of claim 19, wherein the wind direction values measured along the survey path comprise wind direction values relative to the vehicle, and wherein determining the representative wind direction according to the wind direction values measured along the survey path comprises converting wind direction values relative to the vehicle into wind direction values relative to ground, and determining the representative wind direction according to the wind direction values relative to ground.

21. A method comprising:

employing a computer system comprising at least one processor to group a plurality of measured natural gas concentration peaks into a collection assigned to a single natural gas leak, the peaks being defined by natural gas concentration data measured by a mobile gas concentration measurement device carried by a vehicle along a survey path, the vehicle carrying a positioning device configured to determine geospatially-referenced locations of gas concentration measurement points along the survey path, the vehicle further carrying a wind direction determination device configured to measure wind direction values along the survey path, wherein grouping the plurality of peaks is performed according to an inter-peak distance determined according to geospatially-referenced locations measured by the positioning device, and further according to a representative wind direction characterizing a measurement of the natural gas concentration data, the representative wind direction being determined according to the wind direction values measured along the survey path; and employing the computer system to select for display a subset of representative peaks characterizing the natural gas leak, wherein the collection includes at least one peak not selected as a representative peak for display.

22. The method of claim 21, wherein the wind direction values measured along the survey path comprise wind direction values relative to the vehicle, and wherein determining the representative wind direction according to the wind direction values measured along the survey path comprises converting wind direction values relative to the vehicle into wind direction values relative to ground, and determining the representative wind direction according to the wind direction values relative to ground.

23. A computer system comprising at least one processor and associated memory configured to:

group a plurality of measured natural gas concentration peaks into a collection assigned to a single natural gas leak, the measured natural gas concentration peaks being defined by natural gas concentration data measured by a mobile gas concentration measurement device carried by a vehicle along a survey path, the vehicle carrying a positioning device configured to determine geospatially-referenced locations of gas concentration measurement points along the survey path, the vehicle further carrying a wind direction determination device configured to measure wind direction values along the survey path; and select for display a set of representative peaks characterizing the natural gas leak, wherein the collection includes at least one peak not selected as a representative peak for display, wherein selecting for display the set of representative peaks comprises at least one of:
identifying a highest-amplitude peak in the collection, and in response, selecting the highest-amplitude peak for display;
identifying a most-upwind peak in the collection, and in response, selecting the most-upwind peak for display; and
identifying at least one peak in the collection that meets a predetermined amplitude threshold, and in response, selecting the at least one peak for display.

24. The computer system of claim 23, wherein the predetermined amplitude threshold has a value between 1 ppm and 20 ppm above a local background.

25. The computer system of claim 23, wherein selecting for display the set of representative peaks comprises at least two of:
identifying the highest-amplitude peak in the collection, and in response, selecting the highest-amplitude peak for display;
identifying the most-upwind peak in the collection, and in response, selecting the most-upwind peak for display; and
identifying at least one peak in the collection that meets a predetermined amplitude threshold, and in response, selecting the at least one peak for display.

26. A non-transitory computer-readable medium encoding instructions which, when executed by a computer system comprising at least one processor, cause the at least one processor to:
group a plurality of measured natural gas concentration peaks into a collection assigned to a single natural gas leak, the measured natural gas concentration peaks being defined by natural gas concentration data measured by a mobile gas concentration measurement device carried by a vehicle along a survey path, the vehicle carrying a positioning device configured to determine geospatially-referenced locations of gas concentration measurement points along the survey path, the vehicle further carrying a wind direction determination device configured to measure wind direction values along the survey path; and
select for display a set of representative peaks characterizing the natural gas leak, wherein the collection includes at least one peak not selected as a representative peak for display, wherein selecting for display the set of representative peaks comprises at least one of:
identifying a highest-amplitude peak in the collection, and in response, selecting the highest-amplitude peak for display;
identifying a most-upwind peak in the collection, and in response, selecting the most-upwind peak for display; and
identifying at least one peak in the collection that meets a predetermined amplitude threshold, and in response, selecting the at least one peak for display.

27. The non-transitory computer-readable medium of claim 26, wherein the predetermined amplitude threshold has a value between 1 ppm and 20 ppm above a local background.

28. The non-transitory computer-readable medium of claim 26, wherein selecting for display the set of representative peaks comprises at least two of:
identifying the highest-amplitude peak in the collection, and in response, selecting the highest-amplitude peak for display;
identifying the most-upwind peak in the collection, and in response, selecting the most-upwind peak for display; and
identifying at least one peak in the collection that meets a predetermined amplitude threshold, and in response, selecting the at least one peak for display.

29. A method comprising:
employing a computer system comprising at least one processor to group a plurality of measured natural gas concentration peaks into a collection assigned to a single natural gas leak, the measured natural gas concentration peaks being defined by natural gas concentration data measured by a mobile gas concentration measurement device carried by a vehicle along a survey path, the vehicle carrying a positioning device configured to determine geospatially-referenced locations of gas concentration measurement points along the survey path, the vehicle further carrying a wind direction determination device configured to measure wind direction values along the survey path; and
employing the computer system to select for display a set of representative peaks characterizing the natural gas leak, wherein the collection includes at least one peak not selected as a representative peak for display, wherein selecting for display the set of representative peaks comprises at least one of:
identifying a highest-amplitude peak in the collection, and in response, selecting the highest-amplitude peak for display;
identifying a most-upwind peak in the collection, and in response, selecting the most-upwind peak for display; and
identifying at least one peak in the collection that meets a predetermined amplitude threshold, and in response, selecting the at least one peak for display.

30. The method of claim 29, wherein the predetermined amplitude threshold has a value between 1 ppm and 20 ppm above a local background.

31. The method of claim 29, wherein selecting for display the set of representative peaks comprises at least two of:
identifying the highest-amplitude peak in the collection, and in response, selecting the highest-amplitude peak for display;
identifying the most-upwind peak in the collection, and in response, selecting the most-upwind peak for display; and
identifying at least one peak in the collection that meets a predetermined amplitude threshold, and in response, selecting the at least one peak for display.

* * * * *